US011837071B2

(12) United States Patent
Zaima et al.

(10) Patent No.: US 11,837,071 B2
(45) Date of Patent: Dec. 5, 2023

(54) SYSTEM AND METHOD FOR MONITORING HAND HYGIENE, WELLNESS, AND HUMAN INTERACTIONS

(71) Applicant: Sterilogy Holdings, Inc., Bloomfield Hills, MI (US)

(72) Inventors: Harold Zaima, Bloomfield Hills, MI (US); John Kreitz, Beverly Hills, MI (US)

(73) Assignee: Sterilogy Holdings, Inc., Bloomfield Hills, MI (US)

( * ) Notice: Subject to any disclaimer, the term of this patent is extended or adjusted under 35 U.S.C. 154(b) by 52 days.

(21) Appl. No.: 17/399,991

(22) Filed: Aug. 11, 2021

(65) Prior Publication Data

US 2022/0051546 A1 Feb. 17, 2022

Related U.S. Application Data

(60) Provisional application No. 63/064,879, filed on Aug. 12, 2020.

(51) Int. Cl.
*G08B 21/24* (2006.01)
*G08B 21/04* (2006.01)

(52) U.S. Cl.
CPC ....... *G08B 21/245* (2013.01); *G08B 21/0453* (2013.01)

(58) Field of Classification Search
CPC .. G08B 21/245; G08B 21/0453; G16H 40/20; G16H 40/67
See application file for complete search history.

(56) References Cited

U.S. PATENT DOCUMENTS

| 2007/0229288 A1 | 10/2007 | Ogrin et al. |
| 2009/0091458 A1 | 4/2009 | Deutsch |
| 2010/0128753 A1* | 5/2010 | Claypool ................ G01K 1/14 |
| | | 374/102 |

(Continued)

FOREIGN PATENT DOCUMENTS

| KR | 102134903 B1 | 7/2020 | |
| WO | WO-2013106440 A1 * | 7/2013 | ........... A47K 5/1202 |

OTHER PUBLICATIONS

International Search Report and Written Opinion dated Dec. 3, 2021 corresponding to International Application No. PCT/US2021/045685, 12 pages.

(Continued)

*Primary Examiner* — An T Nguyen
(74) *Attorney, Agent, or Firm* — Harness, Dickey & Pierce, P.L.C.

(57) ABSTRACT

A system includes a bed zone boundary module and a user interface device (UID) control module. The bed zone boundary module is configured to detect when at least one of a first wearable dispenser assembly and an identification badge is within a boundary of a zone around a bed, and generate a sanitize reminder signal when at least one of the first wearable dispenser assembly and the identification badge is within the zone boundary. The UID control module is configured to, in response to the sanitize reminder signal, control a user interface device to generate a message reminding a person wearing at least one of the first wearable dispenser assembly and the identification badge to use hand sanitizer before approaching a patient in the bed.

12 Claims, 12 Drawing Sheets

(56) References Cited

U.S. PATENT DOCUMENTS

| | | | | |
|---|---|---|---|---|
| 2010/0315244 | A1* | 12/2010 | Tokhtuev | G16H 40/20 340/603 |
| 2011/0010087 | A1* | 1/2011 | Wons | G06Q 10/06 705/2 |
| 2012/0218106 | A1 | 8/2012 | Zaima et al. | |
| 2014/0367417 | A1* | 12/2014 | Zaima | G16H 40/20 222/175 |
| 2015/0081335 | A1 | 3/2015 | Dixon et al. | |
| 2022/0146320 | A1* | 5/2022 | Xie | G01J 5/0025 |

OTHER PUBLICATIONS

Johnson, Joseph Jr.; Hasan, Shiblee; Lee, David; Hluchan, Chris; and Ahmed, Nazia, "Social-Distancing Monitoring Using Portable Electronic Devices", Technical Disclosure Commons, (Apr. 17, 2020) <https://www.tdcommons.org/dpubs_series/3158>, 9 pages.
Triax Technologies. Proximity Trace, Https://Www.triaxtec.com/Wp-Content/Uploads/2020/06/Proximity-Trace-Overview_Jun. 2020. Pdf, May 2020, 2 pages.

\* cited by examiner

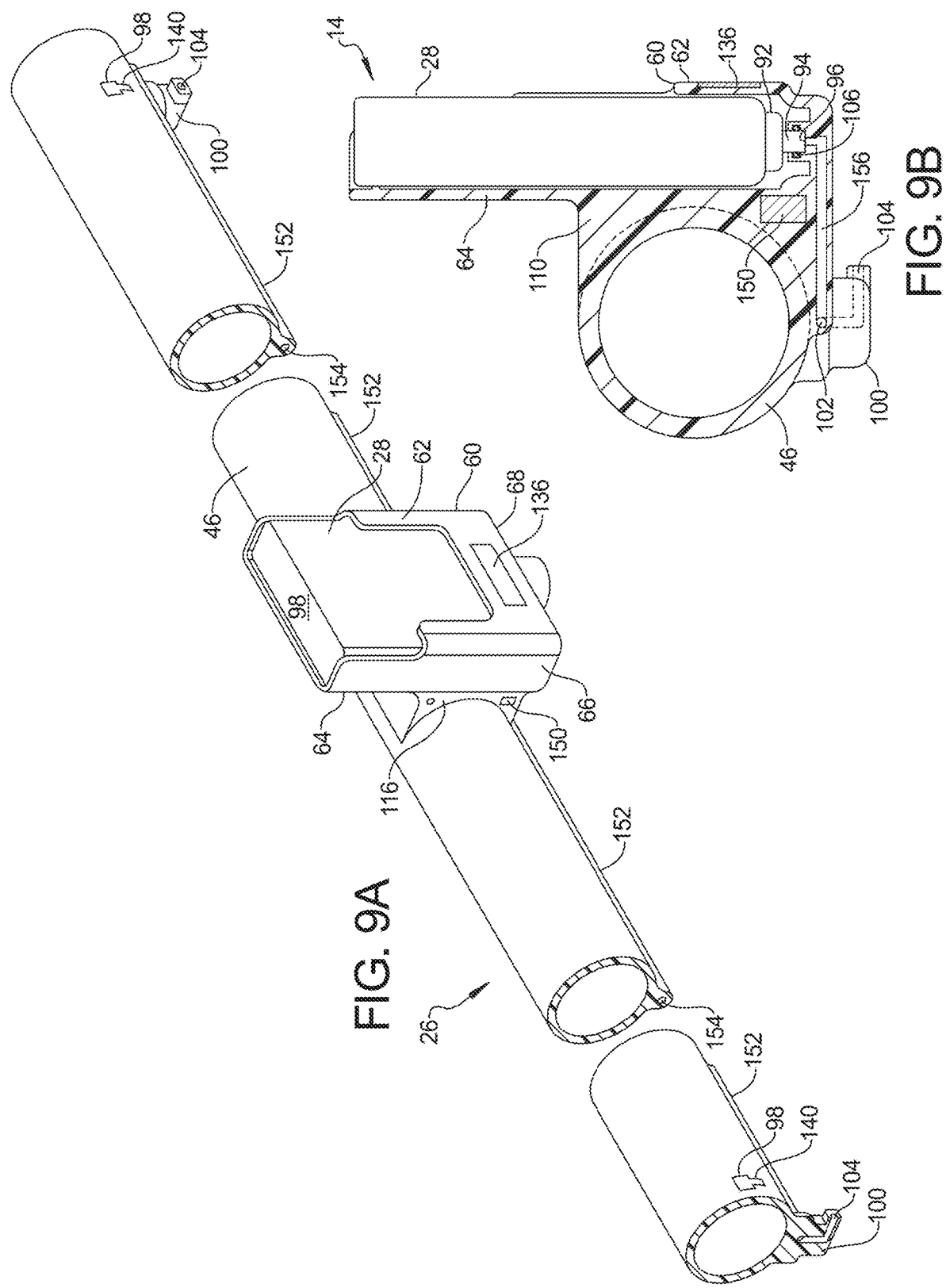

SYSTEM AND METHOD FOR MONITORING HAND HYGIENE, WELLNESS, AND HUMAN INTERACTIONS

CROSS-REFERENCE TO RELATED APPLICATIONS

This application claims the benefit of U.S. Provisional Application No. 63/064,879, filed on Aug. 12, 2020. The entire disclosure of the application referenced above is incorporated herein by reference.

FIELD

The present disclosure relates to systems and methods for monitoring hand hygiene, wellness, and human interaction.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Various infectious diseases such as SARS, Avian Flu, HIV, Herpes, MRSA, H1N1 influenza, and most recently, COVID-19, have had a significant impact on the world population. With the rise of world travelers, such infectious diseases are able to spread more readily from region-to-region and country-to-country, and this pace will only continue to accelerate. Early detection of such infectious diseases and prevention of transmittal are two ways to prevent a widespread epidemic. Also, these infectious diseases are capable of being spread in medical facilities, restaurants, and other public facilities. But in order to stop transmission, the infection must be eradicated at the most widely noted point of transmission. It is well-known that the greatest medium of communication of any bacteria or influenza is through touch. Primarily, this touch is by the hands. Therefore, cleansing the hands frequently and at the appropriate time is essential in the prevention of infectious diseases, most importantly in hospitals where bacteria and pathogens are abundant and where medical practitioners are constantly exposed to such pathogens through contact with patients and the general public.

One method that is available to destroy illness causing pathogens before infection can set in or be transmitted is the use and application of products including anti-microbacterial agents such as ethyl alcohol gels, foam, or liquids. Such products are readily available, are effective in eradicating infectious pathogens from spreading, and kill bacteria upon contact. However, merely having these bacteria killing substances are insufficient. The product must be used, used often, and more importantly used at the correct time. As such, the product must be readily available and the user must use the product at the correct time. Thus, for any disinfecting product to work, the disinfecting substance must be effective, the user must have immediate and convenient access to a device that dispenses the product, and most importantly the disinfecting substance must be applied at the appropriate time.

Currently, medical facilities have multiple locations where medical practitioners can properly cleanse their hands with soap and water. In addition, many medical facilities have stations with antibacterial dispensing containers mounted to the walls. Further, medical practitioners may carry relatively small canisters in their pockets to sterilize their hands prior to each patient examination in order to prevent the transmission of infectious disease. The general public has fewer opportunities to properly and constantly cleanse their hands, with the most common available means being gel pump soap systems found in restrooms of stores and restaurants. Though helpful, none of these methods have proven to be truly effective. In hospitals, the location for properly cleansing the hands with antibacterial soap is not always immediately available. And even if they are available, frequent washing of the hands causes hands to become dry and chaffed resulting in discomfort to both the medical practitioner and the patient.

In the case of gel, liquid, and foam hand sanitizing stations, it must be readily available when the medical practitioner needs or wants to use it. Even if available, often times the medical practitioner finds that the disinfectant at the stations is empty, therefore, constant monitoring and refilling are required. The small canisters are somewhat effective, however, medical practitioners tend to set them down, thereby misplacing them. In order for the cleansing agent to be effective, the method of cleansing the hands within the hospital or in public locations must be convenient and readily accessible at the required point of use.

SUMMARY

An example of a system according to the present disclosure includes a bed zone boundary module and a user interface device (UID) control module. The bed zone boundary module is configured to detect when at least one of a first wearable dispenser assembly and an identification badge is within a boundary of a zone around a bed, and generate a sanitize reminder signal when at least one of the first wearable dispenser assembly and the identification badge is within the zone boundary. The UID control module is configured to, in response to the sanitize reminder signal, control a user interface device to generate a message reminding a person wearing at least one of the first wearable dispenser assembly and the identification badge to use hand sanitizer before approaching a patient in the bed.

In one aspect, the system further includes a dispensing event module configured to determine when a bed dispenser assembly performs a dispensing event by dispensing hand sanitizer, and store a date of the dispensing event and a time of the dispensing event.

In one aspect, the system further includes the bed dispenser assembly, wherein the bed dispenser assembly is one of: separate from the bed and mounted to the bed; and integrated into the bed.

In one aspect, the dispensing event module is configured to associate the dispensing event with at least one of the first wearable dispenser assembly and the identification badge.

In one aspect, the dispensing event module is configured to generate a dispensing event signal indicating the date and time of the dispensing event, and at least one of the first wearable dispenser assembly and the identification badge includes a tracking module configured to receive the dispensing event signal and to store the date and time of the dispensing event.

In one aspect, the dispensing event module is configured to store a location of the bed at the time of the dispensing event.

In one aspect, the bed zone boundary module is configured to detect when the first wearable dispenser assembly is within the zone boundary, detect when a second wearable dispenser assembly is within the zone boundary, detect when the identification badge is within the zone boundary, and determine which one of the first wearable dispenser assembly, the second wearable dispenser assembly, and the identification badge is closer to the bed dispenser assembly based on a strength of a first signal received from the first wearable dispenser assembly, a strength of a second signal received from the second wearable dispenser assembly, and a strength of a third signal received from the identification badge, and the dispensing event module is configured to associate the dispensing event with the one of the first wearable dispenser assembly, the second wearable dispenser assembly, and the identification badge that is closer to the bed at the time of the dispensing event.

Another example of a system according to the present disclosure includes a room identification module and a bed location module. The room identification module is configured to generate a room identification signal indicating an identification of a room in a healthcare facility. The bed location module is configured to receive the room identification signal and, in response to the room identification signal, associate a first bed with the room identification. The bed location module is further configured to store a date on which the first bed is associated with the room identification and a time at which the first bed is associated with the room identification.

In one aspect, the system further includes a bed identification module configured to generate a first bed identification signal indicating an identification of the first bed, and the room identification module is configured to receive the first bed identification signal and determine a location of the first bed within the room based on a strength of the first bed identification signal.

In one aspect, the system further includes a second bed identification module configured to generate a second bed identification signal indicating an identification of a second bed, and the room identification module is configured to receive the second bed identification signal, compare a strength of the second bed identification signal to the first bed identification signal and, based on the comparison, determine the location of the first bed within the room and a location of the second bed within the room.

In one aspect, the system further includes a bed zone boundary module configured to detect when at least one of a wearable dispenser assembly and an identification badge is within a boundary of a zone around the first bed, and selectively generate a sanitize reminder signal when at least one of the wearable dispenser assembly and the identification badge is within the zone boundary.

In one aspect, the bed zone boundary module is configured to generate the sanitize reminder signal when (i) at least one of the wearable dispenser assembly and the identification badge is within the zone boundary and (ii) the room ID signal is received.

In one aspect, the bed zone boundary module is configured to stop generating the sanitize reminder signal when the room ID signal is no longer received.

In one aspect, the bed zone boundary module is configured to resume generating the sanitize reminder signal when the room ID signal is received for at least a predetermined period.

Yet another example of a system according to the present disclosure includes a wearable dispenser location module and a dispending event module. The wearable dispenser location module is configured to determine a location of a wearable dispenser assembly. The dispensing event module is configured to detect when the wearable dispenser assembly performs a dispensing event by dispensing hand sanitizer, and store a date of the dispensing event, a time of the dispensing event, and the location of the wearable dispenser assembly at the time of the dispensing event.

In one aspect, the system further includes a UID control module configured to control a user interface device to display the date and time of the dispensing event and the location of the wearable dispenser assembly at the time of the dispensing event.

In one aspect, the system further includes a tracking module configured to determine when a person wearing the wearable dispenser assembly has made a stop and a duration of the stop, and the UID control module is configured to control the user interface device to display the duration of the stop.

In one aspect, the system further includes a temperature probe control module configured to control a temperature probe to measure a temperature of a person wearing the wearable dispenser assembly.

In one aspect, the system further includes a UID control module configured to control a user interface device to display the temperature of the person and the time at which the temperature of the person is measured.

In one aspect, the UID control module is configured to prompt the person wearing the wearable dispenser assembly to perform a temperature check when a period that has elapsed since a last temperature check is greater than a predetermined period.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 9A is a partially sectioned perspective view of an example of a bed-integrated dispenser assembly according to the principles of the present disclosure;

FIG. 9B is a sectioned side view of the bed-integrated dispenser assembly of FIG. 9A;

In the drawings, reference numbers may be reused to identify similar and/or identical elements.

DETAILED DESCRIPTION

Figure 1:
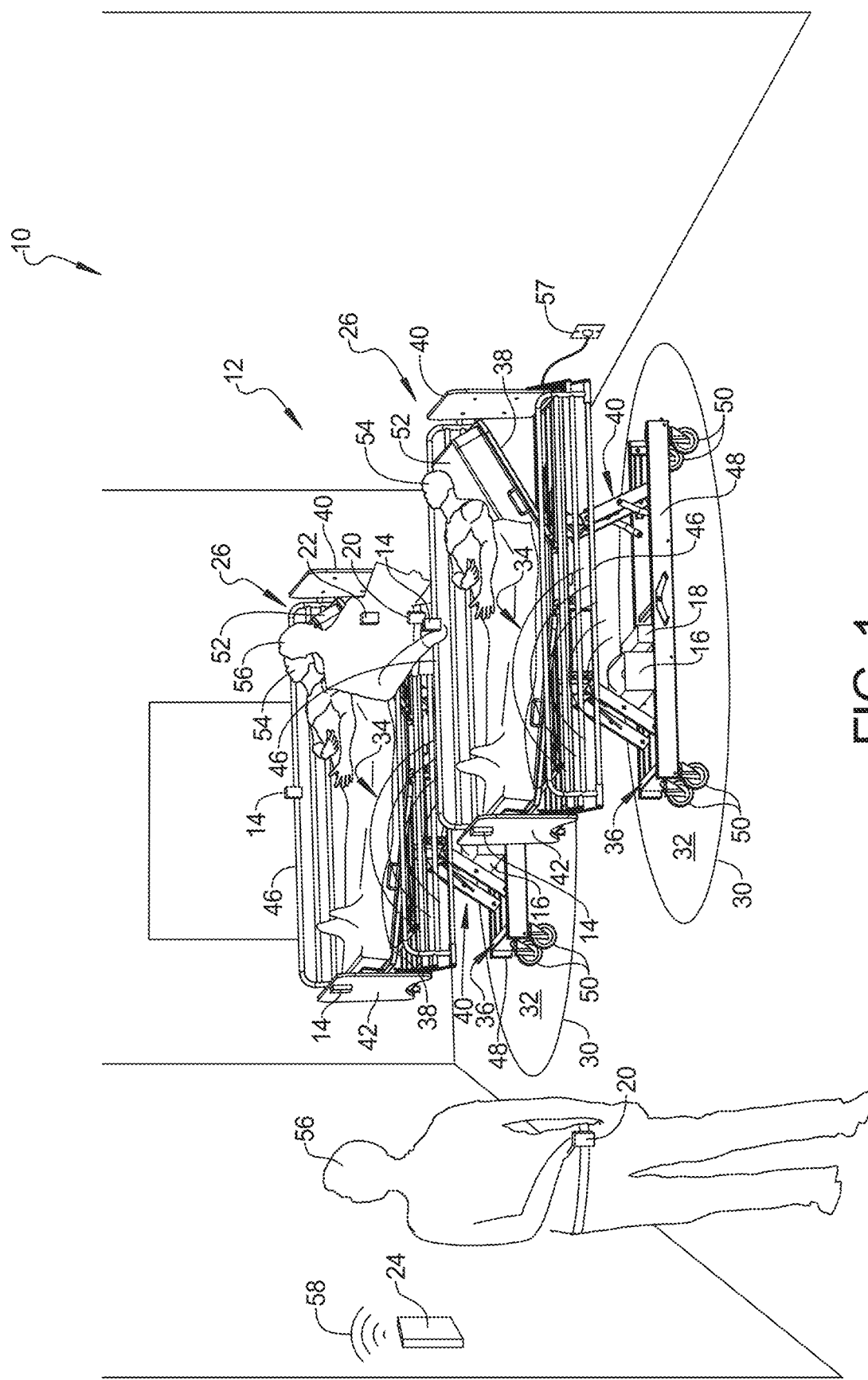
FIG. 1 is a perspective view of a healthcare facility room incorporating an example of a system for monitoring hand hygiene, wellness, and human interaction according to the principles of the present disclosure.

Referring now to FIG. 1, a healthcare facility room 10 includes a system 12 for monitoring hand hygiene, wellness, and human interaction. The system 12 includes bed dispenser assemblies 14, bed zone boundary modules 16, backup batteries 18 (only one shown), wearable dispenser assemblies 20, an identification badge 22, and a room identification (ID) module 24. The bed dispenser assemblies 14 may be integrated into beds 26 in the room 10, or the bed dispenser assembly 14 may be separate from the beds 26 and mounted thereto. Each bed dispenser assembly 14 is configured to contain a fluid and to dispense a portion of the fluid in response to an action by a user such a pressing a button or surface of the bed dispenser assembly 14. The fluid may be a liquid, gel, lotion, gas, or foam such as disinfectant fluid (e.g., sanitizer) or another fluid or fluid-like substance or light such as ultraviolet light. In addition to or instead of being configured to dispense fluid, each bed dispenser assembly 14 may be configured to illuminate a disinfectant light, such as ultraviolet light, onto hands to disinfect the hands. Each act or instance of dispensing fluid or illuminating a disinfectant light as described above is referred to herein as a dispensing event.

Each bed zone boundary module 16 is configured to detect when one or more of the wearable dispenser assemblies 20 and the identification badge 22 is/are within a boundary 30 of a zone 32 around the respective bed 26 (i.e., the bed 26 on which the bed zone boundary module 16 is mounted). Each bed zone boundary module 16 accomplishes this by wirelessly communicating with the wearable dispenser assemblies 20 and the identification badge 22 using, for example, WiFi, ultra-wideband (UWB), Bluetooth, or radio-frequency identification (RFID). In one example, each bed zone boundary module 16 outputs a scanning signal 34, and each of the wearable dispenser assemblies 20 and the identification badge 22 outputs a feedback signal in response to the scanning signal 34. In this example, each bed zone boundary module 16 may determine that one of the wearable dispenser assemblies 20 and the identification badge 22 is within the zone boundary 30 of the respective bed 26 when that bed zone boundary module 16 receives the feedback signal from that one of the wearable dispenser assemblies 20 and the identification badge 22. Thus, the zone boundary 30 may represent the maximum range of the scanning signal 34 and/or the feedback signal.

In the example shown, each bed 26 includes a base 36, a platform 38, an incline adjustment mechanism 40, a headboard 42, a footboard 44, and a pair of side rails 46. The bed dispenser assemblies 14, the bed zone boundary modules 16, and/or the backup batteries 18 may also be considered part of the beds 26. The base 34 includes a frame 48 and wheels 50 that enable moving the beds 26 from one location to another location. The platform 38 is configured to support a mattress 52 on which a patient 54 may lie. The incline adjustment mechanism 40 connects the platform 38 to the base 36 and includes an actuator for adjusting the angle of the platform 38 relative to horizontal. In various implementations, the incline adjustment mechanism 40 may be replaced with a static structure that connects the platform 38 to the base 36 and does not include a mechanism for adjusting the angle of the platform 38 relative to horizontal. Each bed zone boundary module 16 is mounted on the base 36 of the respective bed 26. A distance between each bed zone boundary module 16 and the footboard 44 of the respective bed 26 is equal to about one-third of the length of the respective bed 26.

Each bed zone boundary module 16 communicates with the bed dispenser assembly 14 of the respective bed 26 via a wired connection or a wireless connection (e.g., WiFi, UWB, Bluetooth, RFID). For example, each bed dispenser assembly 14 may inform the bed zone boundary module 16 of the respective bed 26 when that bed dispenser assembly 14 dispenses fluid. In another example, each bed zone boundary module 16 generates a sanitize reminder signal when one of the wearable dispenser assemblies 20 or the identification badge 22 is within the zone boundary 30 of the respective bed 26. In response to the sanitize reminder signal, the bed dispenser assembly 14 of the respective bed 26 displays a message reminding a person 56 wearing one of the wearable dispenser assemblies 20 or the identification badge 22 to sanitize their hands before approaching the respective bed 26. Additionally or alternatively, in response to the sanitize reminder signal, each wearable dispenser assembly 20 displays a message reminding a person 56 wearing the respective wearable dispenser assembly 20 to sanitize their hands before approaching the respective bed 26. In various implementations, each bed zone boundary module 16 may not generate a sanitize reminder signal if the wearer of the wearable dispenser assembly 20 or the identification badge 22 within the boundary 30 of the respective bed 26 sanitizes their hands before entering the zone 32.

Each backup battery 18 supplies power to a respective bed 26 (i.e., the bed 26 on which the backup battery 18 is mounted) when an alternating current (AC) power supply to the respective bed 26 is interrupted. For example, each backup battery 18 may supply power to the respective bed 26 when the respective bed 26 is disconnected from an AC power source 57, which is depicted as a wall outlet of the healthcare facility room 10. Each backup battery 18 may supply power to the entire electrical system of the respective bed 26 to operate, for example, the bed dispenser assembly 14, the bed zone boundary module 16, and the incline adjustment mechanism 40. Alternatively, each backup battery 18 may supply power to only the bed zone boundary module 16. When the AC power supply to the bed 26 is restored, the backup battery 18 may recharge using the AC power supply. The backup battery 18 may include an antiovercharge mechanism.

Each wearable dispenser assembly 20 is configured to be worn by a person such as either one of the persons 56 shown in FIG. 1. In addition, each wearable dispenser assembly 20 is configured to contain a fluid and to dispense a portion of the fluid in response to an action by a user such a pressing a button or surface of the wearable dispenser assembly 20. The fluid may be a liquid, gel, lotion, gas, or foam such as disinfectant fluid (e.g., sanitizer) or another fluid or fluid-like substance. Further, each bed zone boundary module 16 wirelessly communicates with each wearable dispenser assembly 20. For example, as discussed above, each bed zone boundary module 16 may determine that one of the wearable dispenser assemblies 20 is within the zone boundary 32 of the respective bed 26 when that bed zone boundary module 16 receives the feedback signal from that wearable dispenser assembly 20.

In another example, each bed zone boundary module 16 may determine which one of the wearable dispenser assemblies 20 is closest to the respective bed dispenser assembly 14 based on the strengths of the signals received from the wearable dispenser assemblies 20. More specifically, each bed zone boundary module 16 may determine that the one of the wearable dispenser assemblies 20 with greatest signal strength is closest to the respective bed dispenser assembly 14. Then, when one of the bed dispenser assemblies 14 dispenses fluid, the bed zone boundary module 16 on the respective bed 26 may credit the person 56 wearing the wearable dispenser assembly 20 that is closest to that bed dispenser assembly 14 for the dispensing event. In other words, the bed zone boundary module 16 may attribute the dispensing event to the person 56 wearing the wearable dispenser assembly 20 that is closest to the respective bed dispenser assembly 14.

The identification badge 22 is configured to wirelessly communicate with the bed zone boundary modules 16 using, for example, WiFi, UWB, Bluetooth, or RFID. For example, as discussed above, each bed zone boundary module 16 may determine that the identification badge 22 is within the zone boundary 32 of the respective bed 26 when that bed zone boundary module 16 receives the feedback signal from the identification badge. In another example, each bed zone boundary module 16 may determine which one of the wearable dispenser assemblies 20 and the identification badge 22 is closest to the respective bed dispenser assembly 14 based on the strength of the signals received therefrom. Then, when one the bed dispenser assemblies 14 dispenses fluid, the bed zone boundary module 16 on the respective bed 26 may credit the person 56 wearing the one of the wearable dispenser assemblies 20 or the identification badge 22 that is closest to the respective bed dispenser assembly 14 for the dispensing event.

In various implementations, the wearable dispenser assemblies 20 and the identification badge 22 may wirelessly communicate with the bed dispenser assembly 14 directly instead of or in addition to communicating with the bed dispenser assembly 14 through the bed zone boundary module 16. For example, each bed zone boundary module 16 may send a signal to the bed dispenser assembly 14 on the respective bed 26 indicating which one of the wearable dispenser assemblies 20 or the identification badge 22 is closest to the bed dispenser assembly 14. Then, when the bed dispenser assembly 14 on the respective bed 26 dispenses fluid, that bed dispenser assembly 14 may credit the person 56 wearing the one of the wearable dispenser assemblies 20 or the identification badge 22 that is closest thereto for the dispensing event.

The room ID module 24 communicates with the bed dispenser assemblies 14 and/or the bed zone boundary modules 16 using a wireless connection (e.g., WiFi, UWB, Bluetooth, RFID). In one example, the room ID module 24 generates a room identification signal 58 indicating an identification of the room 10 such as a room number. When the bed zone boundary modules 16 receive the room identification signal 58, the bed zone boundary modules 16 associate the respective bed 26 (i.e., the bed 26 on which that bed zone boundary module 16 is mounted) with the identification of the room 10. In addition, the bed zone boundary modules 16 may store a date on which the respective bed 26 is associated with the room identification and a time at which the respective bed 26 is associated with the room identification. In this manner, the bed zone boundary modules 16 tracks the healthcare facility room(s) in which the beds 26 are located, as well as when the beds 26 are located in the room(s). In turn, the location of the patients 54 within a healthcare facility may be tracked by using the locations of the beds 26 as a proxy or surrogate for the locations of the patients 54.

Various elements shown in FIG. 1 may be omitted, and the other elements may still function as described herein to the extent possible without the omitted elements. For example, while the system 12 is shown as including two wearable dispenser modules 20 and two beds 26, the system 12 may include only one wearable dispenser module 20 and/or only one bed 26. In another example, a healthcare worker entering the room 10 does not necessarily have to wear the wearable dispenser module 20, as the bed dispenser assembly 14 provides the healthcare worker with the option of using the bed dispenser assembly 14 or the wearable dispenser module 20 to sanitize. In this example, the healthcare worker may wear the identification badge 22 in order to receive credit for the dispensing event. The bed dispenser assembly 14 may also lower the healthcare facility's sanitizer cost.

In various implementations, one or more elements of each bed 26, such as the bed dispenser assembly 14 and/or the bed zone boundary module 16, may be included in a mobile transport device (e.g., stretcher, wheelchair) or in a head wall structure attached to the wall behind the bed 26. In these implementations, the location of the mobile transport device or the head wall structure may serve as a surrogate for the location of the patient. In other implementations, the bed zone boundary module 16 may be included in a device (e.g., a wristband) that is worn by the patient or a device that is implanted in the patient to always provide a precise location of the patient.

Referring now to FIGS. 2 through 7, an example implementation of the wearable dispenser assembly 20 includes a main housing 60 and a container 28 (also referred to as a canister). The main housing 60 includes a front wall 62, a back wall 64, side walls 66 that each extend between the front and back walls 62 and 64, and a bottom wall 68. In the example shown, the front wall 62 and a portion of the side walls 66 form an upper edge 70 having an irregular shape, and each of the front and back walls 62 and 64 is generally curved or arcuate. The front wall 62, the back wall 64, the side walls 66, and the bottom wall 68 together define a cavity 72.

The particular shape, size, and configuration of the main housing 60 may vary. In one embodiment, the main housing 60 may be a claw-type holder. The main housing 60 can be produced from any of numerous materials including, but not limited to, metal or a thermoplastic material. The thermoplastic material may be an anti-bacterial resin such as IonArmour®, antimicrobial masterbatches, or any of a variety of commercially available anti-bacterial resins.

The container 28 is received within the cavity 72 of the main housing 60. The container 28 includes an upper wall 74 and a lower wall 76. The container 28 also includes a front wall 78, a back wall 80, and a pair of side walls 82 extending between the upper and lower walls 74 and 76. In one embodiment, the contour of the front and back walls 78 and 80 of the container 28 is complementary to the curvature of the front and back walls 62 and 64 of the main housing 60 to ensure a proper fit when the container 28 is placed inside the cavity 72 of the main housing 60. It is, however, appreciated that the container 28 may be any of numerous shapes including, but not limited to, cylindrical-shaped, oval-shaped, or crescent-shaped.

The container 28 is secured to the main housing 60 to prevent the inadvertent release of the container 28. The main housing 60 includes a tab 84 formed along a forward surface 86 of the back wall 64. The tab 84 engages a recessed portion formed along the back wall 80 of the container 28 so that the container 28 is securely held within the cavity 72 of the main housing 60. In alternative embodiments, the container 28 is secured using an interference fit or other conventional retaining mechanisms.

When the container 28 is empty, the existing container 28 may be replaced with a new container 28. In order to release the container 28, a user inserts a finger or a similarly-shaped object through at least one aperture 88 formed along the bottom wall 68 of the main housing 60 and pushes against the container 28 to disengage the tab 84 from the recessed portion. As a result, the container 28 is no longer secured to the main housing 60. The tab 84, which is generally tongue-shaped, includes a bottom portion that is attached to the back wall 64 such that the tab 84 flexes back when the container 28 is removed from the main housing 60.

In another embodiment, the side walls 66 of the main housing 60 are formed at a height lower than that of the container 28, which allows the user to grab the container 28 for easy removal and replacement. In other embodiments, one or both of the side walls 66 of the main housing 60 have a depressible finger or tab (not shown) that is generally tongue-shaped and hinged to the main housing 60 to engage an outer surface of the container 28. Upon depressing the tab, a protrusion disposed at a distal end of the tab engages the outer surface to raise the container 28 in the main housing 60 and allow the user to grasp the container 28 and lift it out of the main housing 60.

The container 28 is configured to contain a fluid within an interior 90 (FIG. 7) thereof. The fluid may include liquids, gels, lotions, gases, and foams, such as disinfectant fluids (e.g., sanitizers), and other fluids and fluid-like substances. The container 28 may be pressurized or non-pressurized depending upon the particular fluid that is contained.

Figure 7:
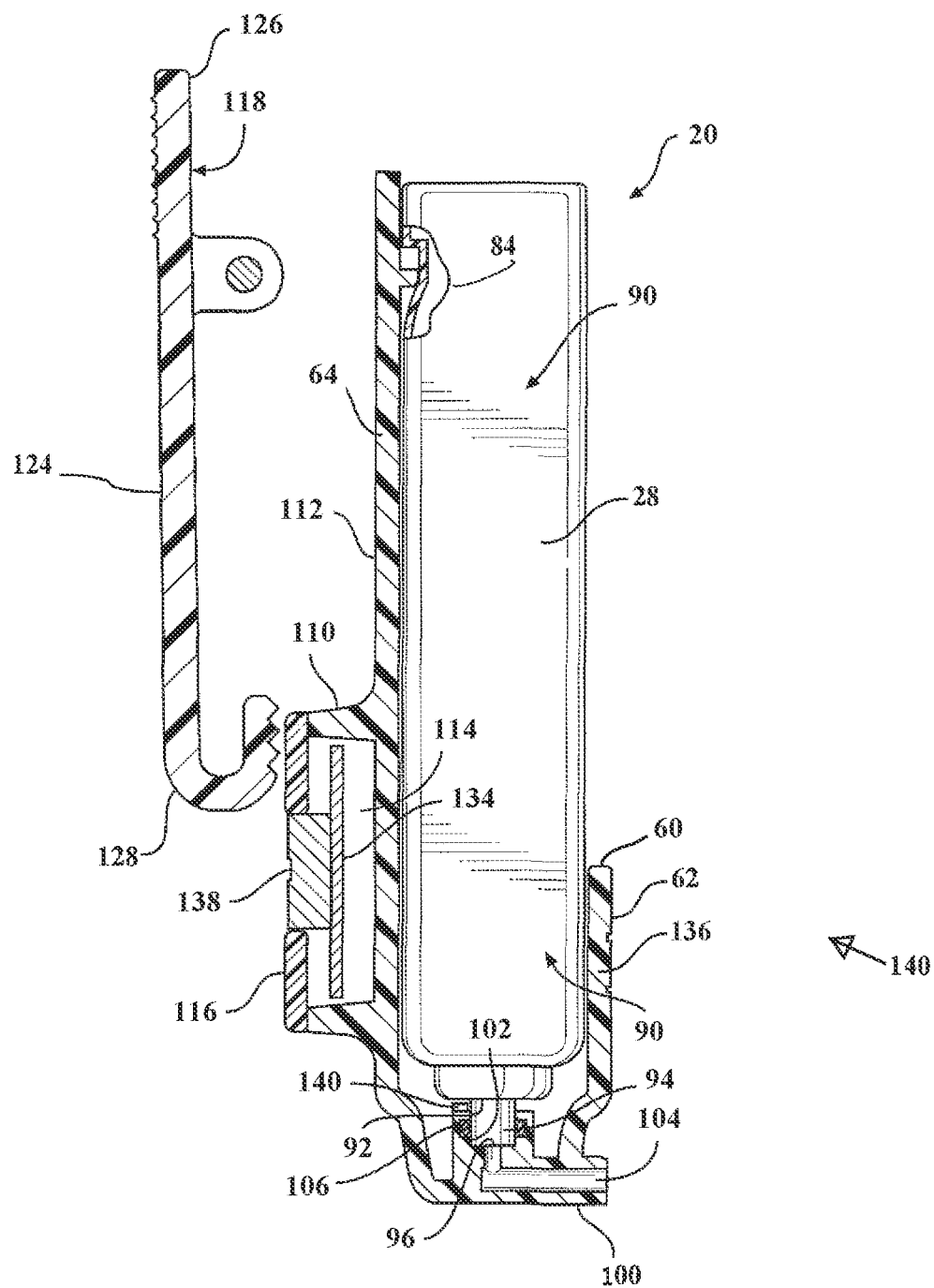
FIG. 7 is a sectioned side view of the wearable dispenser assembly of FIG. 2.

Referring specifically to FIG. 7, the container 28 includes a pump mechanism 92, and a stem 94 disposed within the interior 90 for selectively forcing fluid out of the container 28. The stem 94 is in fluid communication with the interior 90 of the container 28 such that fluid is able to selectively exit the container 28 through an open end 96 of the stem 94. The container 28 includes a depression button 98 (shown in FIG. 2 as a surface) which is pressed downwardly by a user to activate the pump mechanism 92 and force the fluid out of the container 28 through the open end 96 of the stem 94. In some embodiments, the container 28 is an aerosol container in which the pump mechanism 92 is further defined as a valve that is opened by depressing the container 28 relative to the stem 94 against the bias of a valve spring (not shown). Such valves are conventional in the aerosol dispensing container arts and are not described in detail herein. See, for example, the valve system and container in U.S. Pat. No. 6,978,916, which is incorporated herein by reference. In some embodiments, the fluid located in the interior 90 could be dispensed from the container 28 with a pumping dispenser.

With continued reference to FIG. 7, the main housing 60 includes a nozzle 100 extending out from the bottom wall 68. The nozzle 100 is in fluid communication with the stem 94 to selectively eject the fluid from the wearable dispenser assembly 20. The nozzle 100 includes an inlet 102 that is coupled to the open end 96 of the stem 94 to transfer fluid from the interior 90 of the container 28 to the nozzle 100. The nozzle 100 also includes a fluid discharge aperture 104 through which fluid is expelled upon activation of the wearable dispenser assembly 20. The stem 94 is biased back to its normal position by the valve spring (not shown). Since the stem 94 is fixed in position in the nozzle 100, this bias results in the container 28 being biased upwardly to be readied for subsequent use.

A seal 106 is disposed in a groove (not separately numbered) in the nozzle 100. The seal 106 contacts and seals against the stem 94 when the stem 94 of the container 28 is positioned in the nozzle 100. The nozzle 100 is integral with the main housing 60. Alternatively, the nozzle 100 may be separate from the main housing 60 and have wings (not shown) that act as tabs which allow the nozzle 100 to be removed from the main housing 60 and replaced. In alternative embodiments, the nozzle 100 could be screwed into the main housing 60 and be unscrewed to allow the nozzle 100 to be replaced or cleaned as required.

The container 28 is metered. In some embodiments, a mechanism for metering a dose of fluid (not shown) is located within the container 28. In these embodiments, the mechanism comprises an internal assembly as is well known to those skilled in the art for metering out each dose of fluid prior to dispensing so that actuation of the container 28 results in the metered dose being dispensed. If the container 28 is not actuated properly to dispense the entire dose, a partial dose may be dispensed. In this case, a dispensing event may not be recorded. Still, another full dose is metered out for the next dispensing event. In other embodiments, such as when using pump-actuated containers, the meter is set such that a full dose of fluid is dispensed only when the depression button 98 of the container 28 is fully depressed. Fully depressing the depression button 98 resets the container 28 to ensure dispensing of fluid. In either case described above, if the depression button 98 is not fully actuated to dispense a full dose, in some embodiments, the user may not receive credit from the monitoring system, described below, for a dispensing event. The quantity of fluid in the container 28 and the specific metered dosage thereof may be calibrated such that the proper amount is dispensed every time and, depending on the usage rate, the user may only have to replace the container 28 on a periodic basis.

The wearable dispenser assembly 20 may include a metering adjustment device, which ensures that each dispensing of the fluid can be properly adjusted and metered to prevent either too much or too little fluid from being dispensed at one time. The metering adjustment device may be a material that is positioned at the bottom of the main housing 60 that limits how far the container 28 can be depressed, thereby controlling the amount of fluid that is dispensed. In another embodiment, the metering adjustment device includes an adjustable threaded stopper wherein the position of the stopper can be adjusted to ensure that the container 28 bottoms out against the stopper at the right metering position.

The wearable dispenser assembly 20 includes an electric or mechanical counter (not separately numbered) that counts the number of times that fluid has been dispensed (e.g., the number of dispensing events of the wearable dispenser assembly 20). Each time a new container 28 is inserted into the main housing 60, the counter resets and begins to count the number of times that the wearable dispenser assembly 20 has been used. Once the counter reaches a predetermined number, a warning alert is activated (visual, audible, or tactile) to notify the user that it is time to replace the container 28. In the alternative, the warning alert may include a device that is built into the container 28 that produces an audible sound such as a spitting sound when the fluid level is low.

Once the fluid has run out, the empty container 28 is replaced with a full container 28. In an alternative embodiment, the container 28 may include a cover selectively covering a refill opening in a top of the container 28. To refill the container 28, the cover is moved out of the way and fluid is added to the container 28 from a master container via the refill opening.

Figure 2:
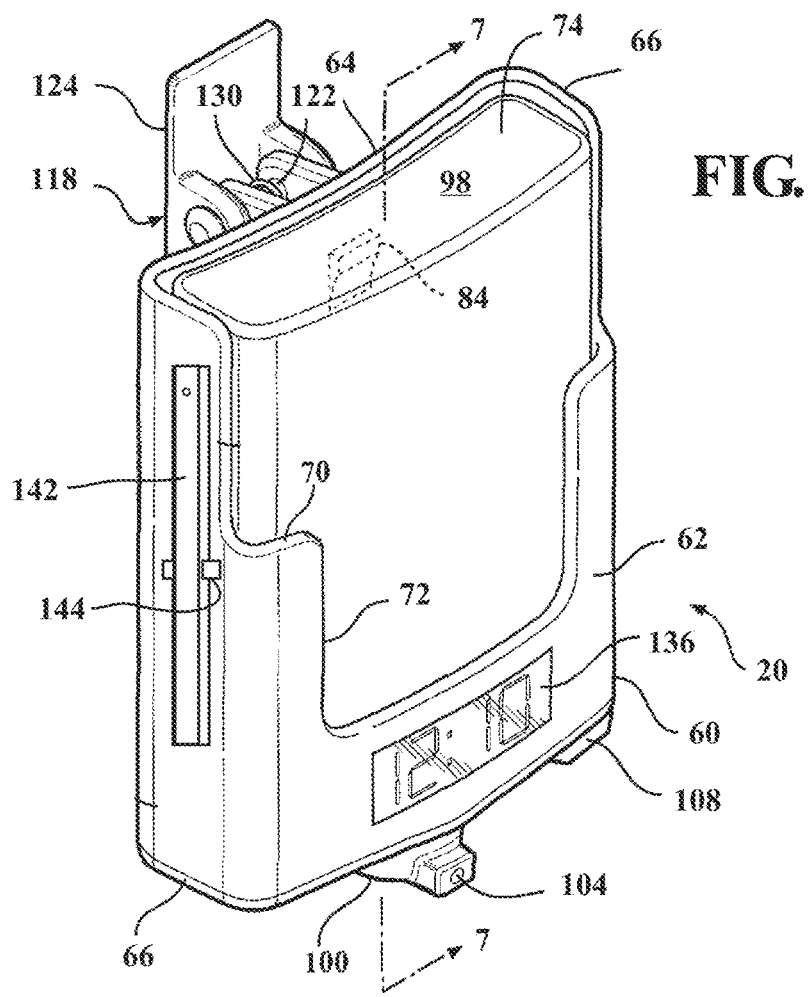
FIG. 2 is a perspective view of an example of a wearable dispenser assembly according to the principles of the present disclosure.
Figure 4:
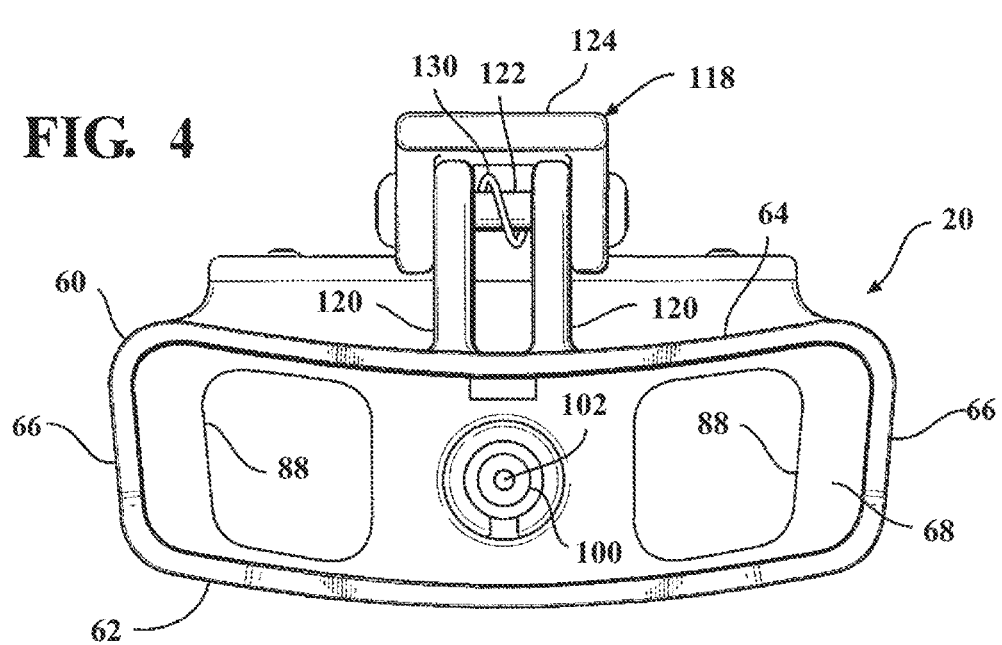
FIG. 4 is a bottom view of the wearable dispenser assembly of FIG. 2.

In one embodiment, a light source 108 is disposed along the bottom wall 68 of the main housing 60, as shown in FIG. 2. The light source 108 may be an ultraviolet, infrared, or similar light source which allows a user to check the effectiveness of the wearable dispenser assembly 20 and associated dispensing events by shining a light onto the area of fluid application and subsequent sanitization to allow the user to ensure the cleanliness of the area of fluid application (e.g., the sanitized area).

Figure 5:
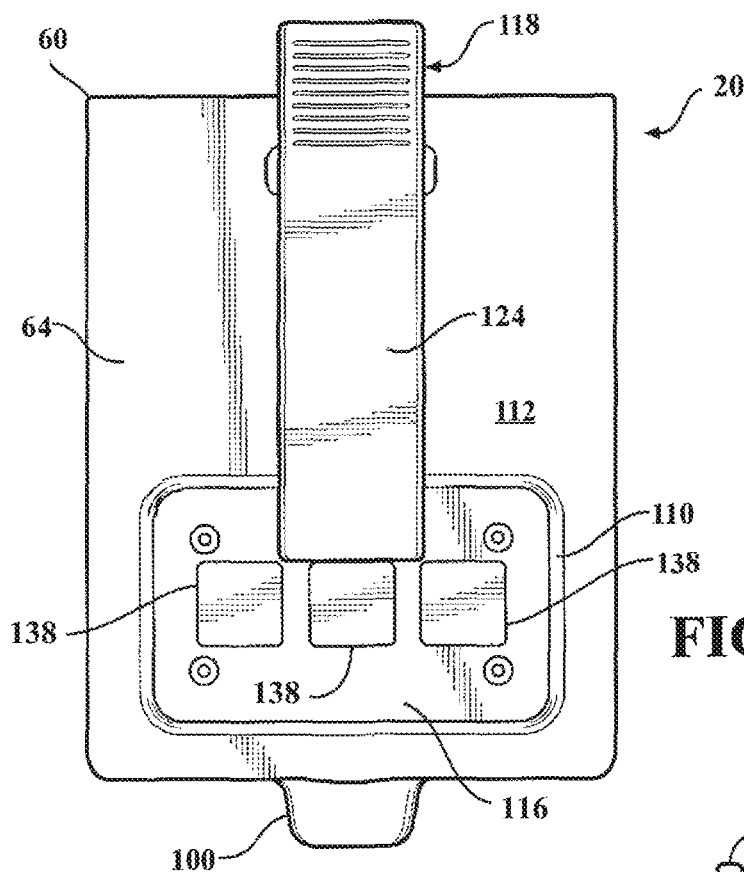
FIG. 5 is a back view of the wearable dispenser assembly of FIG. 2.
Figure 6:
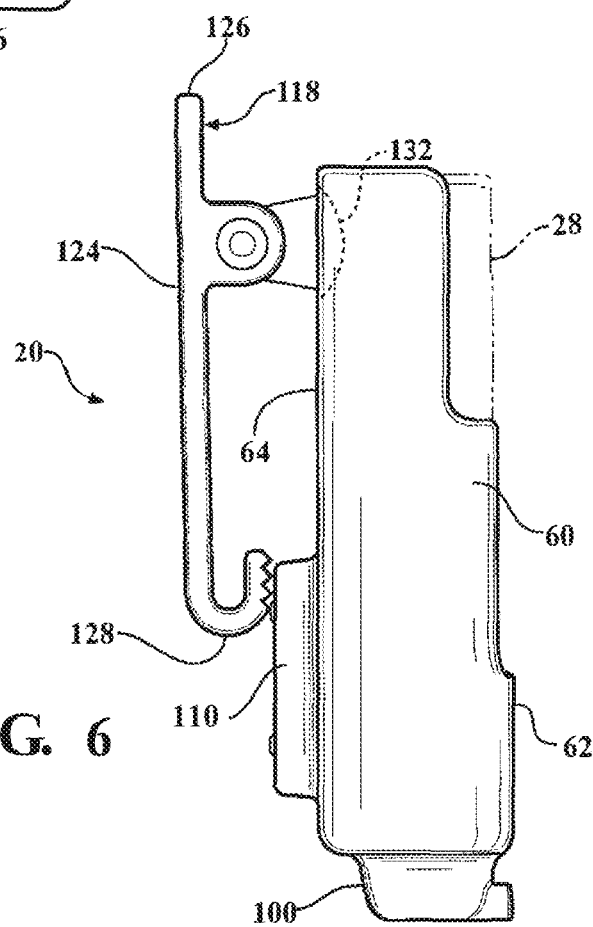
FIG. 6 is a side view of the wearable dispenser assembly of FIG. 2.

Referring to FIGS. 5 through 7, the wearable dispenser assembly 20 includes a flange 110 formed along an outboard surface 112 of the back wall 64 of the main housing 60. The flange 110 and the back wall 64 of the main housing 60 define a chamber 114. The particular location of the chamber 114 relative to the main housing 60 may vary. The chamber 114 is selectively closed by a removable cover 116. The cover 116 may be sealed or unsealed.

Referring now to FIGS. 4 through 7, the wearable dispenser assembly 20 includes a mounting element such as a lanyard (not shown) or a clip assembly coupled to the main housing. The mounting element, allows for attachment of the wearable dispenser assembly 20 to a user's waist belt, lapel, pocket, stethoscope, or the like. In the embodiment shown, the mounting element is a clip assembly 118, which allows for attachment of the wearable dispenser assembly 20 to a user's waist belt, pocket or the like. The clip assembly 118 includes mounting arms 120 extending out from the outboard surface 112 of the back wall 64. A post 122 extends through the mounting arms 120. A clip 124 rotates about the post 122 to move the clip assembly 118 between a closed position, shown in FIG. 6, and an open position. The clip 124 includes an upper end 126 and a lower end 128. In the example shown in FIGS. 4 through 7, the lower end 128 is generally U-shaped or L-shaped. A biasing member 130 is secured to the post 122 for biasing the clip assembly 118 towards the closed position. The biasing member 130 includes ends that abut the back wall 64 and the clip 124 respectively.

In one embodiment, the main housing 60, along with the container 28 secured thereto, may rotate relative to the clip assembly 118 about a base portion 132, as shown in FIG. 6. Thus, a user wearing the wearable dispenser assembly 20 in the standard upright vertical position, i.e., with the depression button 98 forming the uppermost surface of the container 28, may rotate the main housing 60 and container 28 relative to the clip assembly 118 approximately 45 to 90 degrees up to a generally horizontal position such that the depression button 98 is now located along one side of the wearable dispenser assembly 20. As a result, the depression button 98 is less susceptible to contact from a user's stomach, thereby reducing the possibility of accidental dispensing of fluid. It is further appreciated that the user could rotate the main housing 60 and the container 28 to any of numerous use positions from the standard upright vertical position. The base portion 132 may include a click or detent mechanism that clicks into place to let the user know that the main housing 60 and the container 28 are in one of several predetermined positions.

Figure 3:
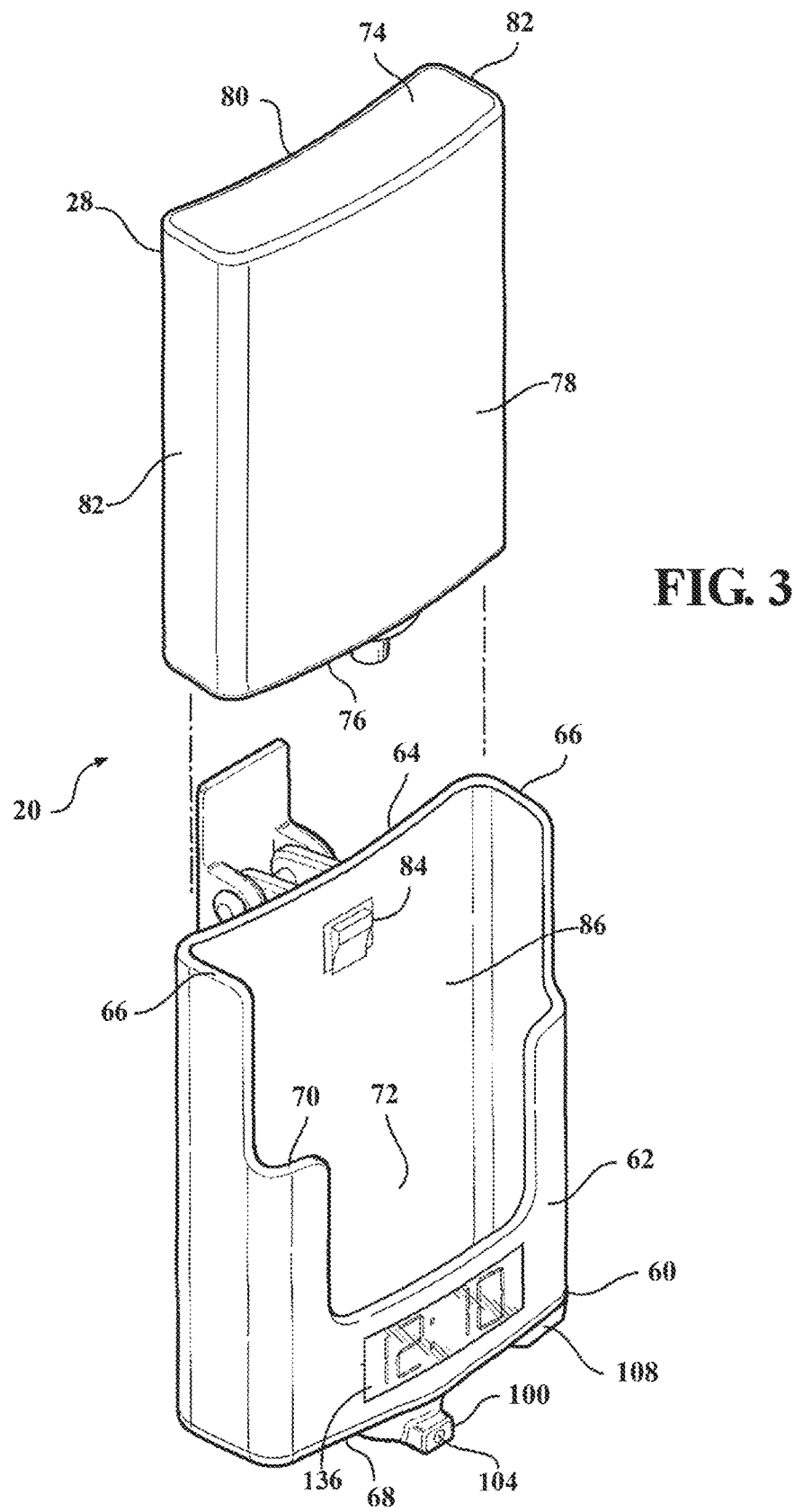
FIG. 3 is an exploded perspective view of the wearable dispenser assembly of FIG. 2.

Referring now to FIGS. 2, 3, and 7, the wearable dispenser assembly 20 further includes a wearable dispenser module 134, an electronic display 136, one or more buttons 138, and an electronic dispensing sensor 140. The electronic display 136 and/or the buttons 138 may collectively makeup or be part of a user interface device. In various implementations, the electronic display 136 may be a touchscreen, in which case the buttons 138 may be omitted. The user interface device may additionally or alternatively include a microphone (not shown), a speaker (not shown) and/or a vibrating mechanism (not shown). The dispensing sensor 140 may also be considered part of the user interface device.

The wearable dispenser module 134 is disposed within the chamber 114. The wearable dispenser module 134 controls the display 136, the speaker, and the vibrating mechanism to generate visual, audible, and tactile messages, respectively. For example, the wearable dispenser module 134 may control the user interface device to generate an alarm (also referred to as a reminder alert) for the user and communicate information to the user regarding the wearable dispenser assembly 20. The wearable dispenser module 134 also collects and transmits data associated with the user and/or dispensing events through a wired or wireless connection.

The display 136 displays alphanumeric characters, graphics, images, and the like. The display 136 may be a light emitting diode display, a liquid crystal display, or another type of display. In the example shown, the display 136 is positioned along the front wall 62 of the main housing 60. However, the display 136 may be positioned in any of various locations on the main housing 60. The display 136 can display the date and time, advertisements, the name of a healthcare facility, the name of a practitioner or user of the wearable dispenser assembly 20, the name of a provider of the disinfectant fluid, or any combination of items.

The buttons 138 are electrically connected to the wearable dispenser module 134. In some embodiments, the buttons 138 extend through the removable cover 116. The buttons 138 operate as an input to the wearable dispenser module 134. The buttons 138 may actuate a switch or other electronic signaling device to provide input to the wearable dispenser module 134. Other input devices could also be used such as a touch-sensitive interface, speech recognition input device, delta-p transducer/sensor, flow sensor, resistive and/or capacitive sensors, and the like.

Upon receiving the alarm, the user may dispense the fluid by, for example, pressing down on the depression button 98 (e.g., the bottom surface of the container 28) to dispense a metered dose of the fluid. After the metered dose of fluid is dispensed, the wearable dispenser module 134 may terminate the alarm. Pressing the depression button 98 actuates the dispensing sensor 140. The dispensing sensor 140 may be a pressure sensor, a flowmeter, a micro switch, or a contact switch that is electrically connected to the wearable dispenser module 134. This dispensing sensor 140 may also be a Hall effect sensor that senses movement of a magnet mounted to the container 28. The dispensing sensor 140 may be located in the main housing 60 beneath the container 28 as shown. The dispensing sensor 140 detects dispensing of the fluid by, for example, detecting movement or depression of the container 28. Alternatively, the dispensing sensor 140 may be a pressure sensor or flow meter placed in proximity of the nozzle 100 to detect pressure changes or flow caused by movement of the fluid through the nozzle 100. The dispensing sensor 140 sends an electrical signal to the wearable dispenser module 134 indicating that a dispensing event has occurred. The wearable dispenser module 134 then records and saves the date, time, and location of the dispensing event.

Referring specifically to FIG. 2, the wearable dispenser assembly 20 further includes a temperature probe 142 and a bracket 144 that holds the temperature probe 142. The wearable dispenser module 134 may control the temperature probe 142 to measure the temperature of a user wearing the wearable dispenser assembly 20. In one example, the user holds the temperature probe 142 against the user's forehead and informs the wearable dispenser module 134 that a temperature check is desired by, for example, pressing one of the buttons 138. In response, the wearable dispenser module 134 controls the temperature probe 142 to measure the temperature of the user. The temperature probe 142 may measure the user's temperature using, for example, infrared. One or more of the buttons 138 may be located on the temperature probe 142. The temperature probe 142 communicates with the wearable dispenser module 134 through a wired or wireless connection.

The bracket 144 projects from one of the sidewalls 66 of the main housing 60. The bracket 144 may hold the temperature probe 142 using an interference fit between the temperature probe 142 and the bracket 144. For example, as the temperature probe 142 is inserted into the bracket 144, arms of the bracket 144 may flex outward (i.e., away from the side surfaces of the temperature probe 142) to enable the temperature probe 142 to be inserted past barbed ends of the arms. Then, when the temperature probe 142 is inserted past the barbed ends, the arms may return to their original positions and the barbed ends may retain the temperature probe 142 in the bracket 144.

Figure 8A:
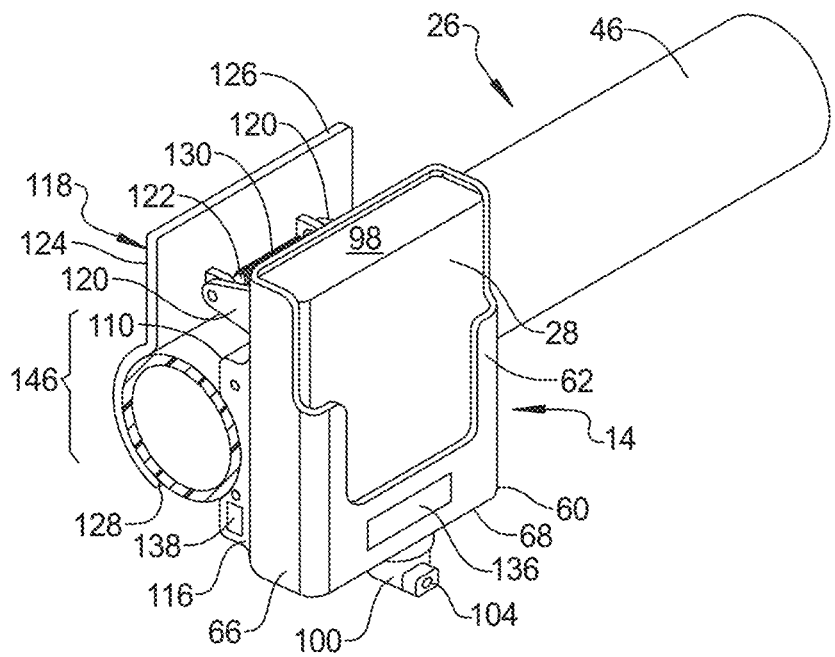
FIG. 8A is a partially sectioned perspective view of an example of a bed-mounted dispenser assembly according to the principles of the present disclosure.
Figure 8B:
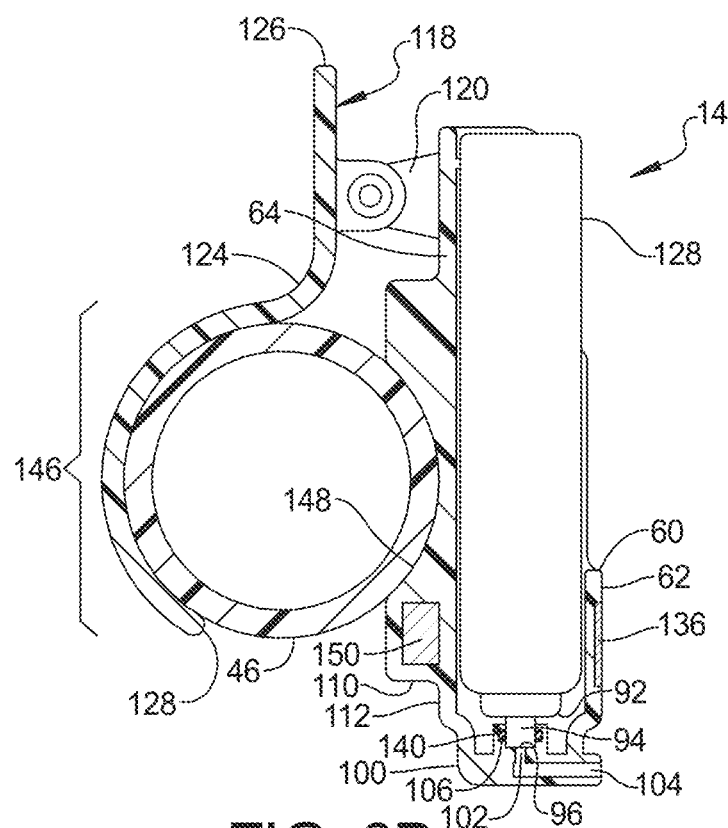
FIG. 8B is a sectioned side view of the bed-mounted dispenser assembly of FIG. 8A.

Referring now to FIGS. 8A and 8B, an example implementation of the bed dispenser assembly 14 and the bed 26 is shown in which the bed dispenser assembly 14 is separate from the bed 26 and mounted to the bed 26. The bed dispenser assembly 14 is substantially similar to the wearable dispenser assembly 20 except that the bed dispenser assembly 14 may be larger than the wearable dispenser assembly 20. Therefore, only differences between the bed dispenser assembly 14 and the wearable dispenser assembly 20 will now be described.

As discussed above, the clip assembly 118 of the wearable dispenser assembly 20 allows for attachment of the wearable dispenser assembly 20 to a user's waist belt, pocket or the like. For example, as best shown in FIG. 6, the lower end 128 of the clip 124 in the wearable dispenser assembly 20 is U-shaped to wrap around a bottom edge of the user's waist belt. In contrast, as shown in FIGS. 8A and 8B, the clip assembly 118 of the bed dispenser assembly 14 allows for attachment of the bed dispenser assembly 14 to one of the side rails 46 of the bed 26. Additionally or alternatively the clip assembly 118 of the bed dispenser assembly 14 may allow for attachment of the bed dispenser assembly 14 to the headboard 42 (FIG. 1) of the bed 26 and/or the footboard 44 (FIG. 1) of the bed 26.

In the example shown in FIGS. 8A and 8B, a lower half 146 of the clip 124 (i.e., the portion of the clip 124 that extends from the lower end 128 of the clip 124 to a point midway between the upper and lower ends 126 and 128 of the clip 124) has a half-cylinder shape that complements the contour the side rail 46. In addition, the clip 124 of the bed dispenser assembly 14 is wider than the clip 124 of the wearable dispenser assembly 20, and the mounting arms 120 of the bed dispenser assembly 14 are spread further apart than those of the wearable dispenser assembly 20 to accommodate the wider clip 124. The wider clip 124 provides additional retention strength and can be implemented with the wearable dispenser assembly 20 since there is no concern regarding the bulkiness of the clip 124 leading to user discomfort.

Further, the flange 110 of the main housing 60 defines a groove 148 that complements the contour of the side rail 46 and receives a portion of the side rail 46 opposite of the portion of the side rail 46 that is receive within the clip 124. Thus, the side rail 46 is clamped firmly between the clip 124 and the flange 110, which inhibits movement of the bed dispenser assembly 14 during a dispensing event. Due to the presence of the groove 148 in the bed dispenser assembly 14, the removable cover 116 and the buttons 138 are relocated from a back surface the flange 110 to a side surface of the flange 110. In addition, the bed dispenser assembly 14 includes a bed dispenser module 150 in place of the wearable dispenser module 134.

The bed dispenser module 150 may be deposed within a chamber (not shown) defined by the flange 110 similar to the chamber 114. The bed dispenser module 150 controls the display 136, the speaker, and the vibrating mechanism to generate visual, audible, and tactile messages, respectively. For example, the bed dispenser module 150 may control the user interface device to generate an alarm (or reminder alert) for a user and communicate information to the user regarding the bed dispenser assembly 14. The bed dispenser module 150 also collects and transmits data associated with the user and/or dispensing events through a wired or wireless connection.

The buttons 138 are electrically connected to the bed dispenser module 150. The buttons 138 operate as an input to the bed dispenser module 150. The buttons 138 may actuate a switch or other electronic signaling device to provide input to the bed dispenser module 150. Other input devices could also be used such as a touch-sensitive interface, speech recognition input device, delta-p transducer/sensor, flow sensor, resistive and/or capacitive sensors, and the like.

Upon receiving the alarm, the user may dispense the fluid by, for example, pressing down on the depression button 98 to dispense a metered dose of the fluid. After the metered dose of fluid is dispensed, the bed dispenser module 150 may terminate the alarm. Pressing the depression button 98 actuates the dispensing sensor 140. The dispensing sensor 140 sends an electrical signal to the bed dispenser module 150 indicating that a dispensing event has occurred. The bed dispenser module 150 then records and saves the date, time, and location of the dispensing event and gives credit for the dispensing event to the wearable dispenser assembly 20 or identification badge 22 worn by the user.

Referring now to FIGS. 9A and 9B, an example implementation of the bed dispenser assembly 14 and the bed 26 is shown in which the bed dispenser assembly 14 is integrated into the bed 26. The bed dispenser assembly 14 of FIGS. 9A and 9B is substantially similar to the bed dispenser assembly 14 of FIGS. 8A and 8B. Therefore, only differences between the bed dispenser assembly 14 of FIGS. 9A and 9B and the bed dispenser assembly 14 of FIGS. 8A and 8B will now be described.

In the bed dispenser assembly 14 of FIGS. 9A and 9B, one of the side rails 46, the main housing 60, and the flange 110 are integrally formed (or formed together) as a single piece. In addition, the clip assembly 118 has been eliminated, as it is not necessary to attach the bed dispenser assembly 14 to the bed 26 using the clip assembly 118 since the bed dispenser assembly 14 is integrated into the bed 26. Further, the bed dispenser assembly 14 includes a pair of nozzles 100 located at opposite ends of the side rail 46 instead of a single nozzle 100 located along the longitudinal centerline of the bed dispenser assembly 14 beneath the bottom wall 68 of the main housing 60. Thus, the bed dispenser assembly 14 enables a user to dispense fluid therefrom at the front or rear end of the bed 26. In various implementations, the bed dispenser assembly 14 may be integrated into the headboard 42 and/or the footboard 44 to enable the user to dispense fluid therefrom at either side of the bed 26.

The side rail 46 includes a U-shaped protrusion 152 projecting downward from the cylindrical portion of the side rail 46, and the longitudinal protrusion 152 defines one or more branch channels 154 that each extend from the main housing 60 to one of the nozzles 100. The main housing 60 and the flange 110 define one or more main channels 156 that deliver fluid from the open end 96 of the container 28 to the branch channels 154. In turn, each branch channel 154 delivers fluid to a respective nozzle 100. The main housing 60 may also include one or more valves (not shown), and the bed dispenser module 150 may control the valves to send fluid through only one of the branch channels 154 to the one of the nozzles 100 where the user is located. Alternatively, a single main channel 156 and a single branch channel 154 may always be filled with fluid from the container 28, and each nozzle 100 may include a valve that is opened by the bed dispenser module 150 to dispense fluid from the respective nozzle 100.

Since the nozzles 100 are located remotely from the container 28 and the main housing 60, the depression button 98 may also be located remotely from the container 28. More specifically, instead of having a single depression button 98 located on (or consisting of) the bottom surface of the container 28, the bed dispenser assembly 14 of FIGS. 9A and 9B includes a pair of depression buttons 98 that are each located at or adjacent to one of the nozzles 100. In addition, the bed dispenser assembly 14 of FIGS. 9A and 9B includes a pair of electronic dispensing sensors 140 that each detect when the respective depression button 98 is pressed by, for example, detecting movement or depression of the button 98.

Figure 10:
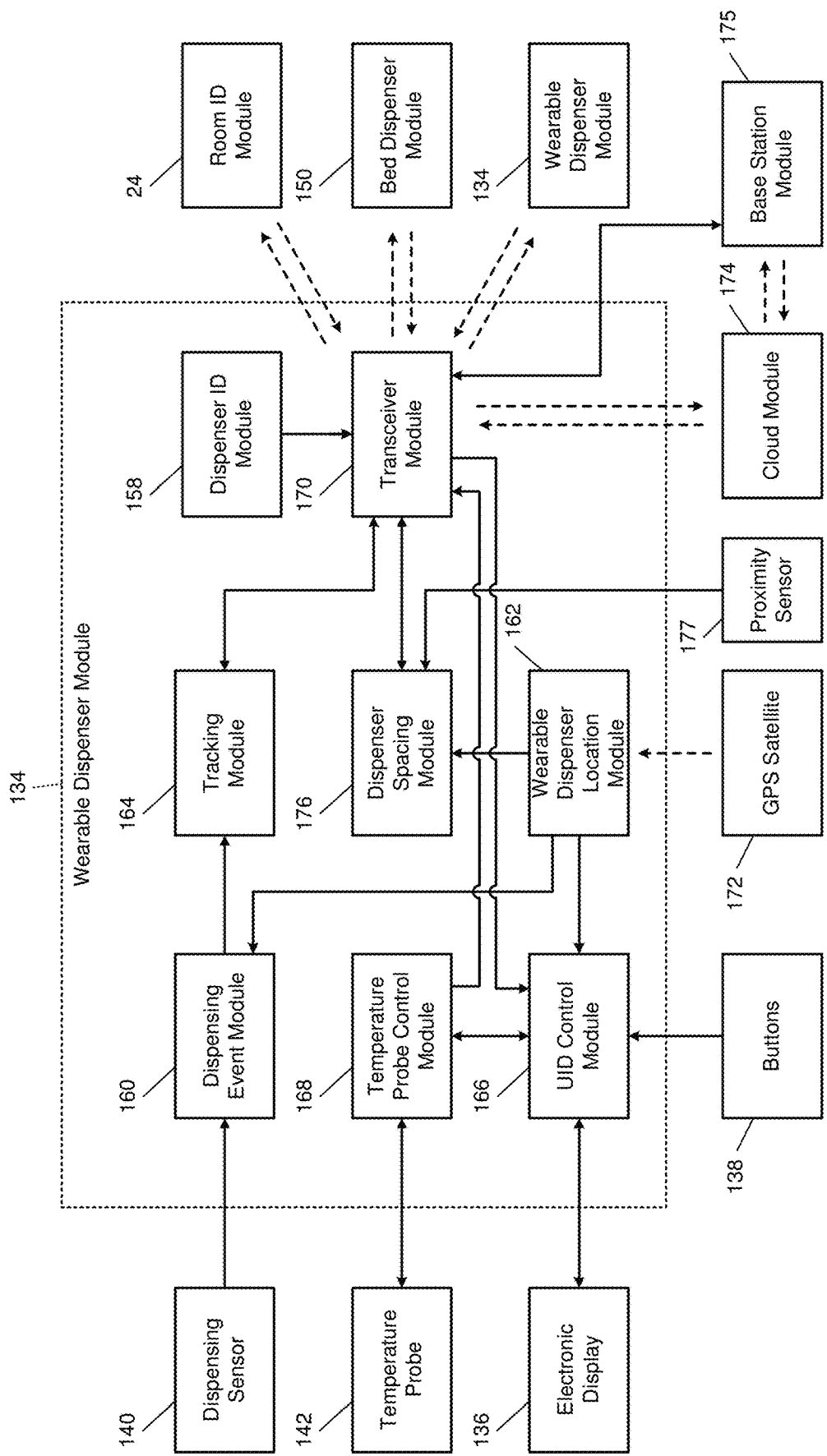
FIG. 10 is a functional block diagram of an example of a wearable dispenser module according to the principles of the present disclosure.

Referring now to FIG. 10, an example implementation of the wearable dispenser module 134 includes a dispenser identification (ID) module 158, a dispensing event module 160, a wearable dispenser location module 162, a tracking module 164, a user interface device (UID) control module 166, a temperature probe control module 168, and a transceiver module 170. The dispenser ID module 158 generates a dispenser ID signal indicating an identification of the respective wearable dispenser assembly 20 (e.g., the wearable dispenser assembly 20 in which the wearable dispenser module 134 is included). For example, the identification may be a unique number that identifies the respective wearable dispenser assembly 20.

The dispensing event module 160 determines when the respective wearable dispenser assembly 20 performs a dispensing event. In addition, the dispensing event module 160 stores the date of the dispensing event, the time of the dispensing event, and the location of the respective wearable dispenser assembly 20 at the time of the dispensing event. Further, the dispensing event module 160 generates (or outputs) a dispensing event signal indicating the date of the dispensing event, the time of the dispensing event, and the location of the respective wearable dispenser assembly 20 at the time of the dispensing event.

In one example, the dispensing event module 160 determines that the respective wearable dispenser assembly 20 has performed a dispensing event when its depression button 98 is pressed for a period that is greater than or equal to a predetermined period. In another example, the dispensing event module 160 determines that the respective wearable dispenser assembly 20 has performed a dispensing event when its depression button 98 is depressed by an amount that is greater than or equal to a predetermined distance. In another example, the dispensing event module 160 determines that the respective wearable dispenser assembly 20 has performed a dispensing event when a change in the pressure in its nozzle 100 or the flow through its nozzle 100 is greater than a predetermine amount. The dispensing event module 160 receives a signal from the dispensing sensor 140 indicating when its depression button 98 is pressed, the amount by which its depression button 98 is depressed, the pressure in its nozzle 100, and/or the flow through its nozzle 100.

The dispensing event module 160 receives the location of the respective wearable dispenser assembly 20 from the wearable dispenser location module 162. The wearable dispenser location module 162 determines the location of the respective wearable dispenser assembly 20 based on GPS signals received from GPS satellites 172, a WiFi access point signal, a cellular tower signal, or a combination thereof. The wearable dispenser location module 162 generates a dispenser location signal indicating the location of the respective wearable dispenser assembly 20.

The tracking module 164 receives the dispensing event signal from the dispensing event module 160 and stores the date of the dispensing event, the time of the dispensing event, and the location of the respective wearable dispenser assembly 20 at the time of the dispensing event. While the dispensing event module 160 may store information related only to the most recent dispensing event, the tracking module 164 may store information related to multiple (e.g., all) dispensing events performed by the respective wearable dispenser assembly 20. The tracking module 164 may also determine when a person wearing the respective wearable dispenser assembly 20 has made a stop and the duration of the stop, and store the date, time, and duration of the stop. For example, using the location of the respective wearable dispenser assembly 20 from the wearable dispenser location module 162, the tracking module 164 may determine when the person makes a stop at a home or healthcare facility along a route passing by several homes and/or healthcare facilities.

In various implementations, the identification badge 22 includes an identification (ID) badge module 171 (FIG. 11) that performs similar to the tracking module 164. The ID badge module 171 may receive a dispensing event signal from the bed dispenser module 150 indicating the date, time, and location of a dispensing event performed by the respective bed dispenser assembly 14. The bed dispenser assembly 150 may transmit the dispensing event signal to the ID badge module 171 to give credit to the respective identification badge 22 for the dispensing event. The ID badge module 171 may store information related to multiple dispensing events for which credit has been given to the respective identification badge 22. The dispensing events may be performed by one or more of the bed dispenser assemblies 14.

The UID control module 166 controls the user interface device (e.g., the electronic display 36, the speaker, and/or the vibrating mechanism) of the respective wearable dispenser assembly 20. For example, the UID control module 166 may control the user interface device to display the current date and time and/or the current location of the respective wearable dispenser assembly 20. In another example, the UID control module 166 may control the user interface device to display the date and time of each dispensing event performed by the respective wearable dispenser assembly 20, as well as the location of the respective wearable dispenser assembly 20 at the time of each dispensing event. In another example, the UID control module 166 may control the user interface device to display the location and duration of each stop made by a person wearing the respective wearable dispenser assembly 20. In another example, the UID control module 166 may control the user interface device to display the temperature of a person wearing the respective wearable dispenser assembly 20 and the time at which the temperature of the person is measured.

In various implementations, the electronic display 136 may be configured to display information to people in the vicinity of the person wearing the respective wearable dispenser assembly 20, and the UID control module 166 may control the electronic display 136 to communicate info to those persons. For example, the UID control module 166 may control the electronic display 136 to display the text "In Compliance" and/or the color green when the period since the wearer last sanitized or checked their temperature is less than or equal to a predetermined period. Conversely, the UID control module 166 may control the electronic display 136 to display the text "Not in Compliance" and/or the color red when the period since the wearer last sanitized or checked their temperature is greater than the predetermined period. In various implementations, the bed dispenser assembly 14, the bed zone boundary module 16, the identification badge 20, and/or a wall-mounted dispenser assembly may include the electronic display 136 and/or the UID control module 166 in addition to or instead of the wearable dispenser assembly 20 including these components.

In addition, the UID control module 166 may receive commands or requests from a user (or wearer) of the respective wearable dispenser assembly 20, and relay those commands or requests to one or more other modules in the wearable dispenser module 134. For example, the user may command a temperature check by touching or speaking to the user interface device of the respective wearable dispenser assembly 20, and the UID control module 166 may relay that command to the temperature probe control module 168. In turn, the temperature probe control module 168 may control the temperature probe 142 to measure the temperature of the user.

In one example, the user holds the temperature probe 142 against the user's forehead and commands a temperature check by, for example, pressing one of the buttons 138. The UID control module 166 then relays that command to the temperature probe control module 168. In another example, the user simply presses one of the buttons 138 to command a temperature check and, in response, the UID control module 166 controls the user interface device to instruct the user to hold the temperature probe 142 against the user's forehead and to press one of the buttons 138 when that is done. When the user completes these tasks, the UID control module 166 relays the command to the temperature probe control module 168.

In yet another example, the temperature probe control module 168 determines whether the period that has elapsed since the last temperature check is greater than a predetermined period (e.g., five minutes). When the elapsed is greater than the predetermined period, the temperature probe control module 168 instructs the UID control module 166 to prompt the person wearing the wearable dispenser assembly to perform a temperature check. The UID control module 166 then follows the instruction by controlling the user interface device to generate a visible message, an audible message, and/or a tactile message.

The transceiver module 170 wirelessly communicates information from modules within the wearable dispenser module 134 to modules outside of the wearable dispenser module 134. In one example, the tracking module 164 outputs a signal indicating the date(s), time(s), and location(s) of one or more dispensing events performed by the respective wearable dispenser assembly 20, and the transceiver module 170 wirelessly transmits that signal to a cloud module 174. In turn, the cloud module 174 stores the dates, times, and locations of the dispensing events. Alternatively, the dispensing event module 160 may output a signal indicating the date, time, and location of the most recent dispensing event performed by the respective wearable dispenser assembly 20, and the transceiver module 170 may wirelessly transmit that signal to the cloud module 174. In this latter example, the cloud module 174 may serve as the tracking module 164 by storing the dates, times, and locations of multiple dispensing events performed by the respective wearable dispenser assembly 20, in which case the tracking module 164 may be omitted.

In various implementations, the tracking module 164 of the wearable dispenser module 134 or the ID badge module 171 (FIG. 11) may transmit a signal to a base station module 175 (FIG. 10). The signal indicates the date(s), time(s), and location(s) of one or more dispensing events performed by the respective wearable dispenser assembly 20 and/or one or more of the bed dispenser assemblies 14. The tracking module 164 may communicate with the base station module 175 via a wired or wireless connection. In one example, the base station module 175 is included in a dongle that connects to a port of a computer in a frequented area, such as a nurse's station near the room 10, and the base station module 175 communicates wirelessly with the wearable dispenser assembly 20 and/or the identification badge 22.

Figure 11:
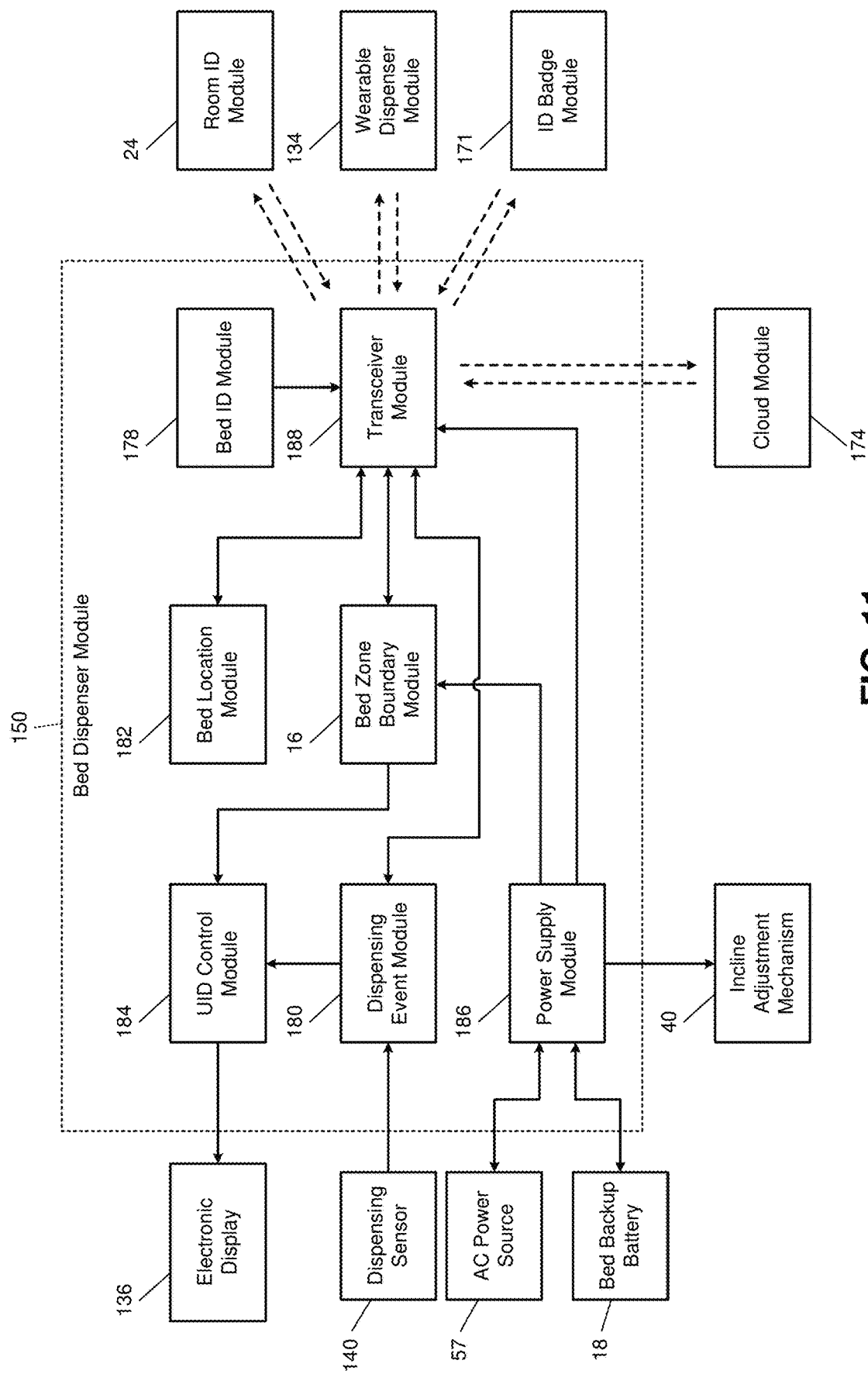
FIG. 11 is a functional block diagram of an example of a bed dispenser module according to the principles of the present disclosure.

In one example, the base station module 175 transmits a ping signal to detect the wearable dispenser assembly 20 or the identification badge 22. When the wearable dispenser assembly 20 or the identification badge 22 connects to the base station module 175 by, for example, returning the ping signal, the base station module 175 retrieves data from the wearable dispenser module 134 or the ID badge module 171 (FIG. 11). The data may include the date(s), time(s), and location(s) of one or more dispensing events performed by the respective wearable dispenser assembly 20 or one of the bed dispenser assemblies 14. The base station module 175 confirms that it has received all of the data and the data is not corrupted, and then the base station module 175 outputs a signal to the wearable dispenser assembly 20 or the identification badge 22 indicating that the data transfer is complete. Additionally or alternatively, the signal may authorize the wearable dispenser assembly 20 or the identification badge 22 to delete the data from its memory to free memory space. The base station module 175 then wirelessly transmits the data to the cloud module 174.

In another example, the tracking module 164 outputs a signal indicating the dates, times, locations, and durations of one or more stops made by a person wearing the respective wearable dispenser assembly 20, and the transceiver module 170 wirelessly transmits that signal to the cloud module 174. The signal output by the tracking module 164 may indicating information related to only the most recent stop, or the signal may indicate information related to multiple stops. In either case, the cloud module 174 may store the dates, times, locations, and durations of multiple (e.g., all) stops made by a person wearing the respective wearable dispenser assembly 20.

In another example, the dispenser ID module 158 outputs the dispenser ID signal indicating the identification of the respective wearable dispense assembly 20 to the transceiver module 170, which wirelessly transmits the dispenser ID signal. With additional reference to FIG. 1, the transceiver module 170 of the other wearable dispenser assembly 20 in the room 10 also wirelessly transmits a dispenser ID signal indicating the identification of that wearable dispenser assembly 20. The room ID module 24 may determine that the wearable dispenser assemblies 20 are in the room 10 when it receives the dispenser ID signals therefrom. The bed dispenser module 150 may determine that the wearable dispenser assemblies 20 are within the zone boundary 30 of the respective bed 26 when it receives the dispenser ID signals therefrom.

The transceiver module 170 also wirelessly communicates information from modules outside of the wearable dispenser module 134 to modules within the wearable dispenser module 134. In one example, the bed dispenser module 150 generates a sanitize reminder signal when the bed dispenser module 150 detects the presence of the wearable dispenser assembly 20 in the room 10 by, for example, receiving the dispenser ID signal. The transceiver module 170 receives the sanitize reminder signal and relays it to the UID control module 166. In response, the UID control module 166 controls the user interface device to generate a message reminding a person wearing the respective wearable dispenser assembly 20 to use hand sanitizer before approaching a patient in the respective bed 26.

The transceiver module 170 also wirelessly communicates information between modules within the wearable dispenser module 134 of the respective wearable dispenser assembly 20 and modules within the wearable dispenser module 134 of the other wearable dispenser assembly 20. In one example, each wearable dispenser module 134 may include a dispenser spacing module 176 that determines the spacing between the respective wearable dispenser assembly 20 and the other wearable dispenser module 20 (or any wearable dispenser assembly 20 or identification badge 22 within range of the respective wearable dispenser assembly 20).

The dispenser spacing module 176 may determine the spacing using a proximity sensor 177, which may be included in each wearable dispenser assembly 20. The dispenser spacing module 176 may determine the spacing based on the location of the respective wearable dispenser assembly 20 from the wearable dispenser location module 162 and the location of the other wearable dispenser module 20 (or the identification badge 22) from the transceiver module 170. The dispenser spacing module 176 may determine the spacing based on the strength of the dispenser ID signal from the other wearable dispenser module 20 (or a badge ID signal from the identification badge 22).

The dispenser spacing module 176 then determines whether the spacing between the wearable dispenser modules 20 (or between the respective wearable dispenser module 20 and the identification badge 22) is less than a predetermined distance (e.g., six feet) for social distancing. If the spacing is less than the predetermined distance, the dispenser spacing module 176 outputs a spacing breach signal indicating that a breach in the spacing between the wearable dispenser modules 20 (or between the respective wearable dispenser module 20 and the identification badge 22) has occurred. In response, the UID control module 166 may control the user interface device to generate a visible, audible, and/or tactile message indicating that the spacing breach has occurred. In addition, the spacing breach signal may indicate the date, time, and location of the spacing breach, as well as the identification of the wearable dispenser module(s) 20 and/or the identification badge 22 that were involved in the spacing breach. The cloud module 174 and/or the dispenser spacing module 176 may store this information for contact tracing purposes.

While the above paragraph describes monitoring social distancing and contact tracing using two wearable dispenser modules 20 or the wearable dispenser module 20 and the identification badge 22, other devices may also be used for this purpose. For example, the wearable dispenser module 20 or the identification badge 22 may interface with a smart phone in a similar manner to monitor social distancing between the wearer of the wearable dispenser module 20 or the identification badge 22 and the user of the smart phone. In addition, the wearable dispenser module 20 or the identification badge 22 may store details regarding the interaction between the wearer and the user, and transmit those details to the cloud module 174 (e.g., directly or via the base station module 175) for contract tracing purposes.

Referring now to FIG. 11, an example implementation of the bed dispenser module 150 includes a bed identification (ID) module 178, a dispensing event module 180, a user interface device (UID) control module 182, a UID control module 184, a power supply module 186, and a transceiver module 188. In this example implementation, the bed dispenser module 150 also includes the bed zone boundary module 16. However, the bed zone boundary module 16 may be separate from the bed dispenser assembly 14 as depicted in FIG. 1. The bed ID module 178 generates a bed ID signal indicating an identification of the respective bed 26 (e.g., the bed 26 in which the bed dispenser module 150 is included). For example, the identification may be a unique number that identifies the respective bed 26.

The dispensing event module 180 determines when the respective bed dispenser assembly 14 (e.g., the bed dispenser assembly 14 in which the bed dispenser module 150 is included) performs a dispensing event. In addition, the dispensing event module 180 stores the date of the dispensing event, the time of the dispensing event, and the location of the respective bed 26 at the time of the dispensing event. Further, the dispensing event module 180 generates (or outputs) a dispensing event signal indicating the date of the dispensing event, the time of the dispensing event, and the location of the respective bed 26 at the time of the dispensing event.

In one example, the dispensing event module 180 determines that the respective bed dispenser assembly 14 has performed a dispensing event when its depression button 98 is pressed for a period that is greater than or equal to a predetermined period. In another example, the dispensing event module 180 determines that the respective bed dispenser assembly 14 has performed a dispensing event when its depression button 98 is depressed by an amount that is greater than or equal to a predetermined distance. In another example, the dispensing event module 180 determines that the respective bed dispenser assembly 14 has performed a dispensing event when a change in the pressure in its nozzle 100 or the flow through its nozzle 100 is greater than a predetermined amount. The dispensing event module 180 receives a signal from the dispensing sensor 140 indicating when its depression button 98 is pressed, the amount by which its depression button 98 is depressed, the pressure in its nozzle 100, and/or the flow through its nozzle 100.

The dispensing event module 180 receives the location of the respective bed 26 in the room 10 from the room ID module 24 via the transceiver module 188. With additional reference to FIG. 1, the room ID module 24 determines the location of the beds 26 in the room 10 based on the strengths of the bed ID signals received therefrom. In one example, the room ID module 24 determines that the bed 26 transmitting the weaker bed ID signal is closest to the window in the room 10, and the room ID module 24 determines that the bed 26 transmitting the stronger bed ID signal is closest to the entrance of the room 10. In the foregoing example, the room ID module 24 may be positioned closer to the entrance of the room 10 to differentiate the strengths of the bed ID signals. The room ID module 24 stores the bed locations and subsequently transmits the bed locations to the wearable dispenser module 134 and/or the badge ID module 171. Additionally or alternatively, the room ID module 24 may store the room identification (e.g., the room number) and, once the bed 26 is located in the room 10, identify the room location of the bed 26 (e.g., window side, hallway side) and transmit that information to the bed zone boundary module 16 of the bed 26. The bed zone boundary module 16 may retain that location until another room ID module 24 sends a new signal identifying a new room identification and room location.

The dispensing event module 180 receives the location of the respective bed 26 in the healthcare facility from the bed location module 182. The bed location module 182 receives the room ID signal from the room ID module 24 via the transceiver module 188. In response to the room ID signal, the bed location module 182 associates the respective bed 26 with the identification of the room 10. In addition, the bed location module 182 stores the date(s) on which the respective bed 26 is associated with the room 10 and the time(s) at which the respective bed 26 is associated with the room 10.

As discussed above with reference to FIG. 1, the bed zone boundary module 16 may generate the sanitize reminder signal when the wearable dispenser assembly 20 or the identification badge 22 is within the zone boundary 30 of the respective bed 26. In one example, the bed zone boundary module 16 only generates the sanitize reminder signal when (i) the wearable dispenser assembly 20 or the identification badge 22 is within the zone boundary 30 of the respective bed 26 and (ii) the bed zone boundary module 16 receives the room ID signal from the room ID module 24. In addition, the bed zone boundary module 16 may stop generating the sanitize reminder signal when (i) the wearable dispenser assembly 20 and the identification badge 22 are not within the zone boundary 30 of the respective bed 26 or (ii) the bed zone boundary module 16 no longer receives the room ID signal. Further, the bed zone boundary module 16 may resume generating the sanitize reminder signal when (i) the wearable dispenser assembly 20 or the identification badge 22 is within the zone boundary 30 of the respective bed 26 and (ii) the bed zone boundary module 16 receives the room ID signal for at least a predetermined period. The bed zone boundary module 16 may deactivate (e.g., power off) when it stops generating the sanitize reminder signal and activate (e.g., power on) when it starts or resumes generating the sanitize reminder signal. The predetermined period may be selected to ensure that the bed zone boundary module 16 is not activated simply by passing the room ID module 24 of the room 10 as the bed 26 is moved down a hallway passing by the room 10.

The UID control module 184 controls the user interface device (e.g., the electronic display 36, the speaker, and/or the vibrating mechanism) of the respective bed dispenser assembly 14. For example, the UID control module 184 may control the user interface device to display the current date and time and/or the current location of the respective bed dispenser assembly 14. In another example, the UID control module 184 controls the user interface device to display the date and time of each dispensing event performed by the respective bed dispenser assembly 14, as well as the location of the respective bed 26 at the time of each dispensing event. The UID control module 184 may receive information related to each dispensing event from the dispensing event module 180. In another example, in response to the sanitize reminder signal from the bed zone boundary module 16, the UID control module 184 controls the user interface device to generate a message reminding a person within the zone boundary 30 to use hand sanitizer before approaching a patient in the respective bed 26. The message may be a visible message, an audible message, and/or a tactile message.

The power supply module 186 detects when the respective bed 26 is disconnected from the AC power source 57. When the respective bed 26 is connected from the AC power source 57, the power supply module 186 supplies power from the AC power source 57 to the bed zone boundary module 16. In addition, the power supply module 186 may supply power from the AC power source 57 to the backup battery 18 of the respective bed 26 to recharge the backup battery 18 of that bed 26.

When the respective bed 26 is disconnected from the AC power source 57, the power supply module 186 supplies power from the bed backup battery 18 to the bed zone boundary module 16. In addition, the power supply module 186 may generate a power interruption signal and, in response, the UID control module 166 may control the user interface device to generate a visible, audible, and/or tactile message indicating that the respective bed 26 is disconnected from the AC power source 57. In addition, the transceiver module 188 may wirelessly transmit the power interruption signal to provide the same notification to healthcare facility staff (e.g., by generating the same message at a nurse's station). In various implementations, when the respective bed 26 is disconnected from the AC power source 57, the power supply module 186 may also supply power from the bed backup battery 18 to the bed dispenser assembly 14 and/or the incline adjustment mechanism 40.

The transceiver module 188 wirelessly communicates information from modules within the bed dispenser module 150 to modules outside of the bed dispenser module 150. In one example, the dispensing event module 180 outputs a signal indicating the date, time, and location of the most recent dispensing event performed by the respective bed dispenser assembly 14, and the transceiver module 188 wirelessly transmit that signal to the cloud module 174. In turn, the cloud module 174 stores the dates, times, and locations of multiple (e.g., all) dispensing events performed by the respective bed dispenser assembly 14. Additionally or alternatively, the transceiver module 188 may wirelessly transmit the signal to the wearable dispenser module 134 or the ID badge module 171 to give credit for the dispensing event to the wearer of the respective wearable dispenser assembly 20 or identification badge 22.

In yet another example, the bed ID module 178 outputs the bed ID signal indicating the identification of the respective bed 26 to the transceiver module 188, which wirelessly transmits the bed ID signal. With additional reference to FIG. 1, the transceiver module 188 of the other bed dispenser assembly 14 in the room 10 also wirelessly transmits a bed ID signal indicating the identification of its respective bed 26. The room ID module 24 determines that the bed dispenser assemblies 14 are in the room 10 when it receives the bed ID signals therefrom. In addition, as discussed above, the room ID module 24 may determine the location of the beds 26 in the room 10 based on the strengths of the bed ID signals received therefrom.

In the description above, the body worn electronics (e.g., the wearable dispenser assembly 20, the identification badge 22) include passive components with low power needs, such as a passive RFID. In contrast, the electronics on the bed 26, mobile transport device, or head wall structure (e.g., the bed dispenser assembly 14, the bed zone boundary module 16) include active components wither higher power requirements such as AC power and/or a large backup battery (e.g., the backup battery 18). However, in various implementations, the locations of the passive and active components may be switched or otherwise different from the locations described above. Likewise, a transceiver module similar or identical to the transceiver modules 170, 188 may or may not be located in the bed dispenser assembly 14, the bed zone boundary module 16, the wearable dispenser assembly 20, and/or the head wall structure.

Also, as indicated above, various information is transmitted to the cloud module 174 such as room identification, bed identification, bed location, date, time, and location of dispensing events (e.g., the identification and/or location of the device that performed the dispensing events), and the wearable dispenser assembly 20 or identification badge 22 credited with the dispensing event. The cloud module 174 may be interoperable with and/or connected to an electronic medical (or health) record (EMR) module (not shown) to enable the collection and analysis of such data on a large scale. For example, the cloud module 174, the EMR module, or an analysis module (not shown) communicating with the cloud module 174 or the EMR module may correlate levels of sanitizer use and noncompliance with a patient's diagnosis, treatments and presence or absence of a hospital acquired infection (HAI). The same module(s) may use the correlation for other patients to predict a high probability of adverse consequences, such as an HAI, and control a user interface device to alert healthcare managers of the prediction so that preventative action may be taken.

Figure 12:
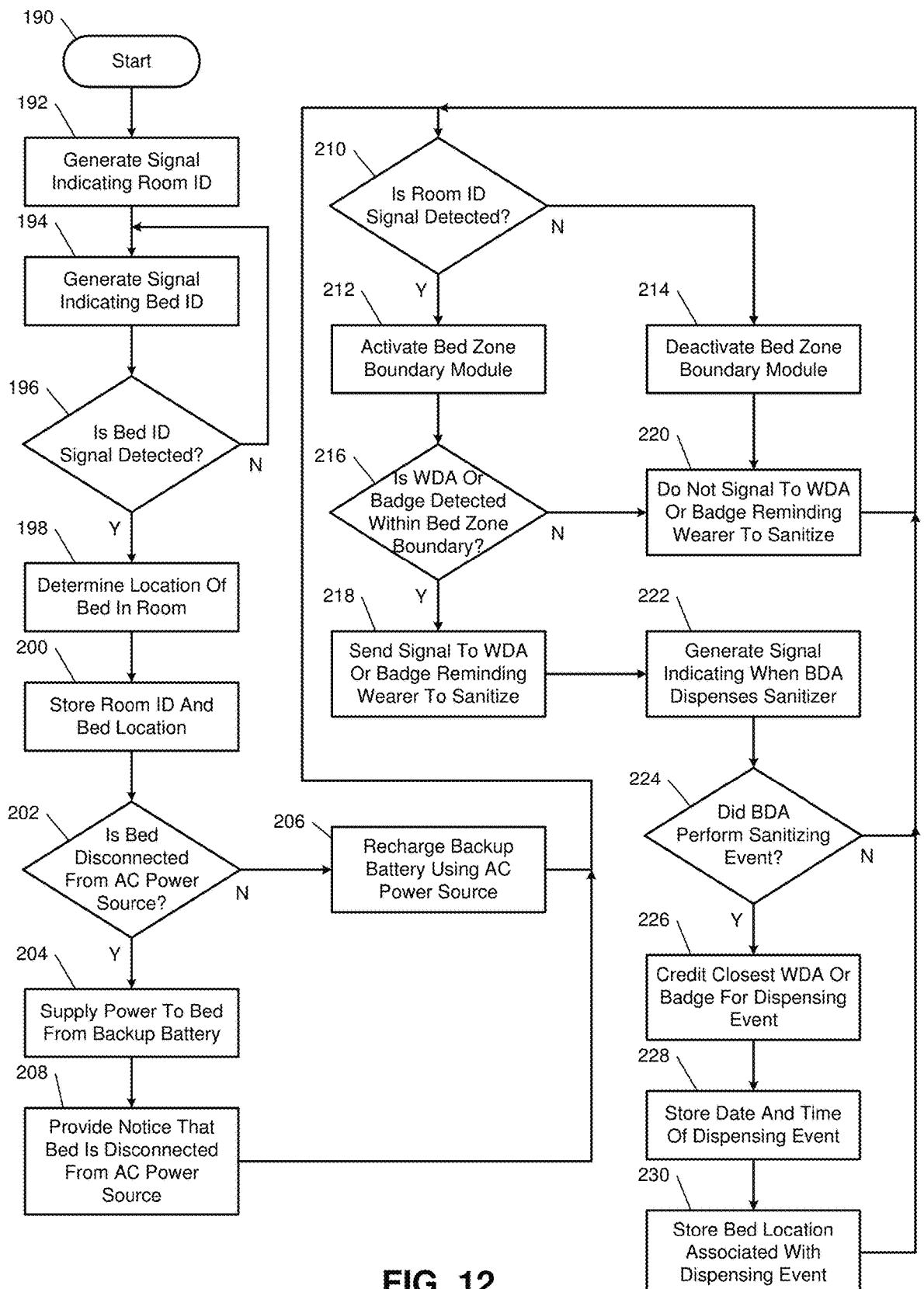
FIG. 12 is a flowchart illustrating an example of a method for monitoring hand hygiene, wellness, and human interaction according to the principles of the present disclosure.

Referring now to FIG. 12, an example method for monitoring hand hygiene, wellness, and human interaction begins at 190. The method is described in the context of the modules of FIGS. 1 and 11. However, the particular modules that perform the steps of the method may be different than the modules mentioned below and/or one or more steps of the method may be implemented apart from any modules.

At 192, the room ID module 24 generates the room ID signal indicating the identification of the room 10. At 194, the bed ID module 178 of each bed dispenser module 150 generates the bed ID signal indicating the identification of the respective bed 26. At 196, the room ID module 24 determines whether it detects (or receives) the bed ID signals. If the bed ID signals are detected, the method continues at 198. Otherwise, the method returns to 194, and the room ID module 24 continues to determine whether the bed ID signals are detected.

At 198, the room ID module 24 determines the locations of the beds 26 in the room 10 based on the strengths of the bed ID signals. For example, the room ID module 24 may determine that the bed 26 with the strongest bed ID signal is closest to the room ID module 24, and the bed 26 with the weakest bed ID signal is furthest away from the room ID module 24. At 200, the bed location modules 182 and/or the cloud module 174 stores the identification of the room 10 and the location of the beds 26 in the room 10. In addition, the bed location modules 182 and/or the cloud module 174 may store the date(s) and time(s) on/at which the beds 26 are located in the room 10 and/or at the particular locations within the room 10.

At 202, the power supply module 186 detects whether the respective bed 26 is disconnected from the AC power source 57. If the respective bed 26 is disconnected from the AC power source 57, the method continues at 204 and the power supply module 186 supplies power to the respective bed 26 from the backup battery 18. At 208, the transceiver module 188 transmits a wireless signal providing notice that the respective bed 26 is disconnected from the AC power source 57. If the respective bed 26 is connected to the AC power source 57, the method continues at 206 and the power supply module 186 recharges the backup battery 18 using the AC power source 57.

At 210, the transceiver module 188 determine whether the room ID signal generated by the room ID module 24, or any room ID module of any room within the healthcare facility, is detected. If the room ID signal is detected, the method continues at 212. Otherwise, the method continues at 214. At 214, the transceiver module 188 deactivates the bed zone boundary module 16. At 220, the transceiver module 188 does not transmit a signal to the wearable dispenser assembly 20 or the identification badge 22 reminding its wearer to sanitize. The method then returns to 210.

At 212, the transceiver module 188 activates the bed zone boundary module 16 of the respective bed 26. In turn, at 216, the bed zone boundary module 16 determines whether the wearable dispenser assembly (WDA) 20 or the identification badge 22 is detected within the zone boundary 30 of the respective bed 26. If the wearable dispenser assembly 20 or the identification badge 22 is detected within the zone boundary 30 of the respective bed 26, the method continues at 218. Otherwise, the method continues at 220. At 218, the transceiver module 188 transmits a signal to the wearable dispenser assembly 20 or the identification badge 22 reminding its wearer to sanitize. Additionally or alternatively, the UID control module 184 may control the user interface (e.g., the electronic display 136) of the respective bed dispenser assembly 14 to remind individuals within the vicinity of the bed 26 to sanitize. In various implementations, at 218, the transceiver module 188 may only transmit a signal to the wearable dispenser assembly 20 or the identification badge 22 reminding its wearer to sanitize if the wearer has not sanitized before entering the zone 32. In these instances, the method may continue from 218 to 228 instead of 222.

At 222, the dispensing sensor 140 generates a signal indicating when the respective bed dispenser assembly (BDA) 14 dispenses fluid. At 224, the dispensing event module 180 determines whether the respective bed dispenser assembly 14 performed a dispensing event. If the respective bed dispenser assembly 14 performed a dispensing event, the method continues at 226. Otherwise, the method returns to 210. In various implementations, the method may return to 216 instead of 210.

At 226, the bed zone boundary module 16 credits the wearable dispenser assembly 20 or the identification badge 22 closest to the respective bed dispenser assembly 14 for the dispensing event. At 228, the dispensing event module 180 and/or the cloud module 174 store(s) the date and time of the dispensing event. If the wearer of the wearable dispenser assembly 20 or the identification badge 22 sanitizes before entering the zone 32, the dispensing event module 180 and/or the cloud module 174 may store the date and time of that dispensing event. At 230, the dispensing event module 180 and/or the cloud module 174 store(s) the location of the bed 26 associated with the dispensing event (e.g., the identification of the room 10, the location of the bed 26 in the room 10). The dispensing event module 180 and/or the cloud module 174 may also store the identification of the wearable dispenser assembly 20 or the identification badge 22 that is credited (or associated) with the dispensing event. If the wearer of the wearable dispenser assembly 20 or the identification badge 22 sanitizes before entering the zone 32, the dispensing event module 180 may still associate or attach the date and time of the dispensing event to the zone 32 of the bed 26 (or of the patient in the bed 26).

Figure 13:
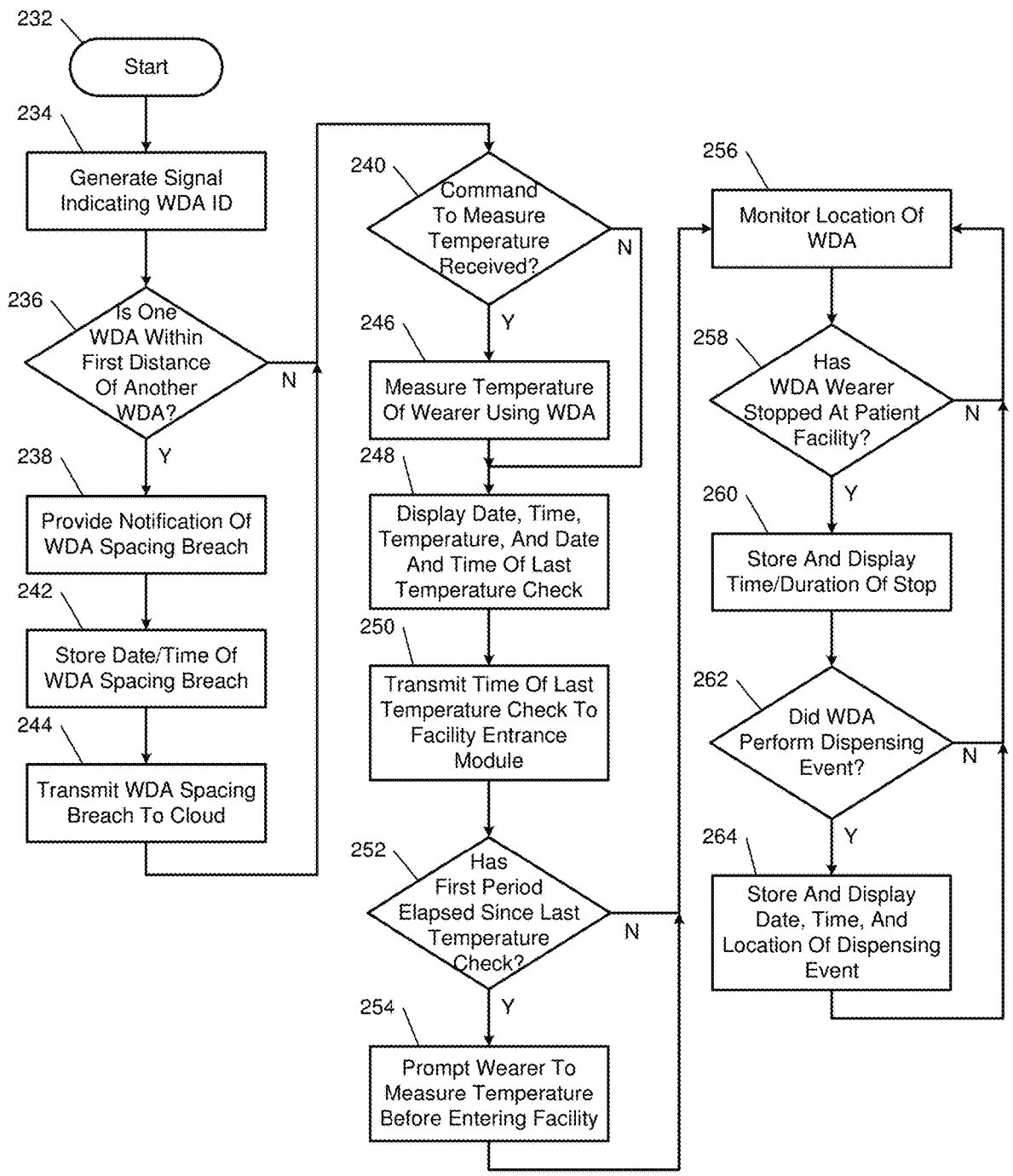
FIG. 13 is a flowchart illustrating another example of a method for monitoring hand hygiene, wellness, and human interaction according to the principles of the present disclosure.

Referring now to FIG. 13, another example method for monitoring hand hygiene, wellness, and human interaction begins at 232. The method is described in the context of the modules of FIGS. 1 and 10. However, the particular modules that perform the steps of the method may be different than the modules mentioned below and/or one or more steps of the method may be implemented apart from any modules.

At 234, the dispenser ID module 158 generates a dispenser ID signal indicating the identification of the respective wearable dispenser assembly 20. At 236, the dispenser spacing module 176 determines whether the respective wearable dispenser assembly 20 is within a first distance of another wearable dispenser assembly 20 (or the identification badge 22). The first distance may be a predetermined distance (e.g., six feet) that achieves social distancing. If the respective wearable dispenser assembly 20 is within a first distance of another wearable dispenser assembly 20 (or the identification badge 22, the method continues at 238. Otherwise, the method continues at 240.

At 238, the dispenser spacing module 176 generates a signal providing notice of the breach in spacing between the wearable dispenser assemblies 20 (or between the wearable dispenser assembly 20 and the identification badge 22). At 242, the dispenser spacing module 176 stores the date and time of the spacing breach. The dispenser spacing module 176 may also store the identifications of the wearable spacing assemblies 20 (or the wearable dispenser assembly 20 and the identification badge 22) involved in the spacing breach. At 244, the transceiver module 170 transmits the above information regarding the spacing breach to the cloud module 174.

At 240, the temperature probe control module 168 determines whether the respective wearable dispenser assembly 20 has received a command to measure the temperature of its wearer. If such a command has been received, the method continues at 246 and the temperature probe control module 168 controls the temperature probe 142 to measure the temperature of the person wearing the respective wearable dispenser assembly 20. Otherwise, the method skips 248 and continues at 248.

At 248, the user interface device of the respective wearable dispenser assembly 20 displays the current date, the current time, the temperature of the person wearing the respective wearable dispenser assembly 20, and the date and time of the last temperature check. At 250, the transceiver module 170 transmits the temperature of the person wearing the respective wearable dispenser assembly 20, and the date and time of the last temperature check, to a facility entrance module (not shown). The facility entrance module may be part of an entrance system (e.g., security or time clock) of a facility (e.g., a manufacturing plant or healthcare facility).

At 252, the facility security module or the temperature probe control module 168 determines whether the period that has elapsed since the last temperature check is greater than a predetermined period (e.g., five minutes). If the elapsed period since the last temperature check is greater than the predetermined period, the method continues at 254. Otherwise, the method skips 254 and continues at 256. At 254, the facility security module or the temperature probe control module 168 instructs the user interface device to prompt the wearer of the respective wearable dispenser assembly 20 to measure his or her temperature before entering the facility.

At 256, the wearable dispenser location module 162 monitors the location of the respective wearable dispenser assembly 20. At 258, the tracking module 164 determines whether the wearer of the respective wearable dispenser assembly 20 has made a stop at a patient facility along a route past several patient facilities. In one example, the tracking module 164 may determine that the wearer has made a stop at a patient facility when the location of the respective wearable dispenser assembly 20 is unchanged for a period that is greater than or equal to a predetermined period. If the wearer has made a stop at a patient facility, the method continues at 260. Otherwise, the method returns to 256. At 260, the tracking module 164 stores the time, date, location, and duration of the stop. In addition, the tracking module 164 may transmit that information to the UID control module 166, which may control the electronic display 136 to display that information. Further, the tracking module 164 may transmit that information to the cloud module 174, which may communicate with an electronic display that displays that information.

At 262, the dispensing event module 160 determines whether the respective wearable dispenser assembly 20 has performed a dispensing event. If the respective wearable dispenser assembly 20 has performed a dispensing event, the method continues at 264. Otherwise, the method returns to 256. At 264, the tracking module 164 and/or the cloud module 174 stores the date, time, and location of the dispensing event. The tracking module 164 and/or the cloud module 174 also communicates with an electronic display (e.g., the electronic display 136), which displays that information.

Figure 14:
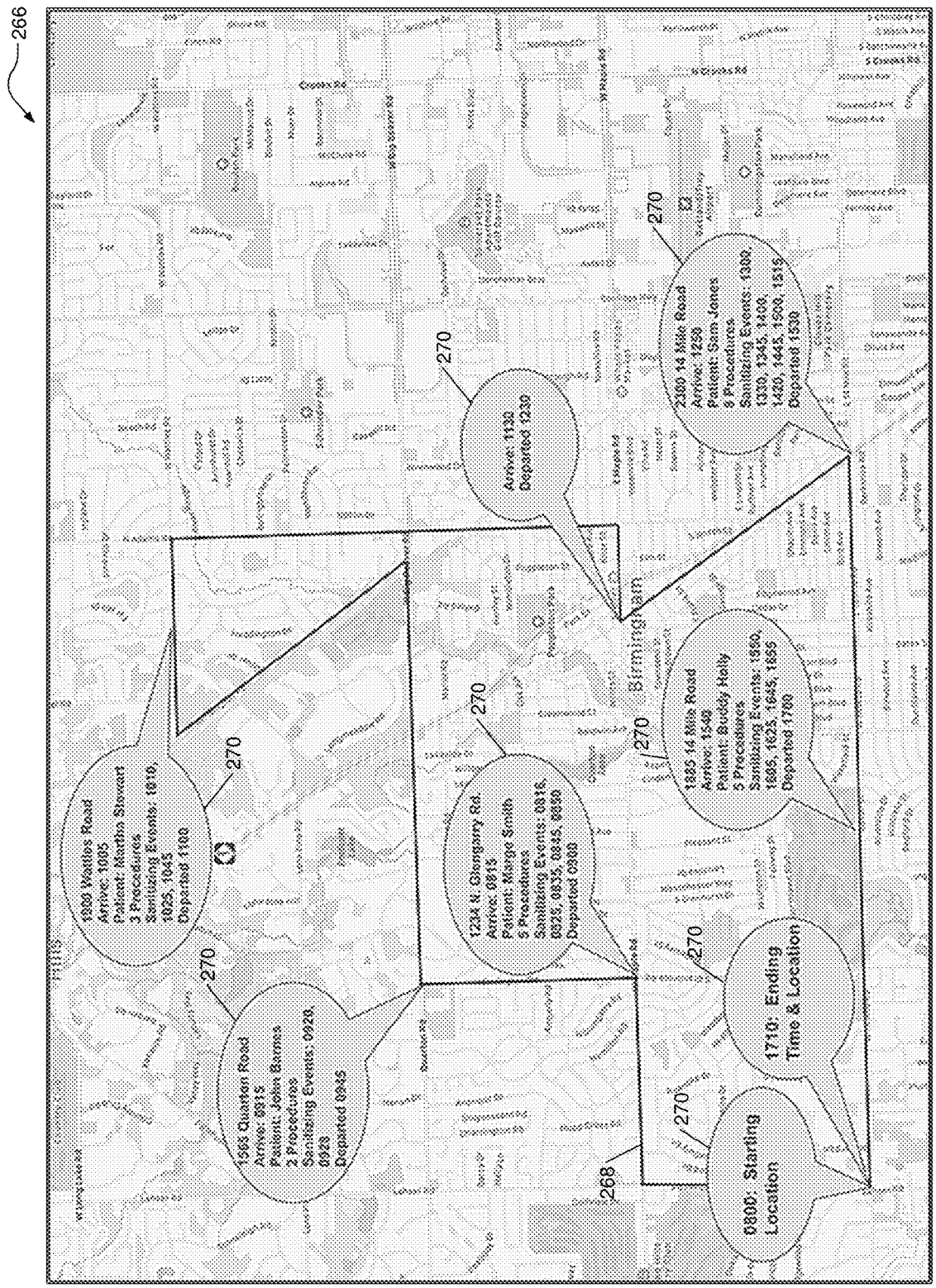
FIG. 14 is a map illustrating an example of information that is displayed in connection with the method of FIG. 13.

FIG. 14 shows example of a map 266 displayed an electronic display to illustrate a route 268 taken by a person wearing the wearable dispenser assembly 20, as well as balloons 270 containing information regarding stops made by the person along the route and dispensing events performed during the stops. Each balloon 270 contains the arrival and departure times of the wearable dispenser assembly 20 associated with the respective stop. In addition, the balloons 270 contain the street address associated with the respective stops, the name of the patients located at that street addresses, and the number of procedures performed during each stop. Further, the balloons 270 also display the times at which the wearable dispenser assembly 20 performed dispensing events (or sanitizing events) during each stop. The information displayed on the map 266 may be wirelessly transmitted from the wearable dispenser assembly 20 to a reimbursement system or module (not shown). The reimbursement module may automatically complete a reimbursement form for the person wearing the wearable dispenser assembly 20 to facilitate efficient and timely reimbursement.

The above description primarily focuses on the functionality of the wearable dispenser assembly 20 and the identification badge 22 in a healthcare setting. However, these devices may also be used in other industries such as the manufacturing industry (e.g., manufacturing plants) and the food industry. With specific regard to the food industry, the public is now especially sensitized to hand hygiene, more now so than in restaurants. Food poisoning or contamination can occur at any step in the food supply chain such as harvesting, production, distribution, groceries, or restaurants. Therefore, the wearable dispenser assembly 20 and the identification badge 22 may be modified to adapt to the specific needs of these environments.

For example, a patron in a restaurant may be equivalent to a patient in a healthcare environment. The patron will likely not be wearing or resting on a targeting device such as the bed dispenser assembly 14. Therefore, locations or "stations" of the food service workers become more important. However, because food service workers repeatedly move from one station to another (e.g., kitchen, bar, expediting line, dining table), even stations (beyond critical ones such as restrooms) may be unsuitable surrogates for driving sanitization events.

Therefore, the wearable dispenser assembly 20 and the identification badge 22 may be modified to generate time-based sanitize reminders rather than location-based or interaction-based sanitize reminders. For example, the wearable dispenser assembly 20 and the identification badge 22 may generate the sanitize reminder signal at predetermined time intervals (e.g., every 20 minutes) regardless of where the food service worker is located. In conjunction with generating the sanitize reminder signal, the wearable dispenser assembly 20 and the identification badge 22 may control a user interface device to generate an audible and/or visible message instructing the food service work to sanitize, wash their hands, or change their gloves.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A system comprising:
   a bed zone boundary module configured to:
     detect when at least one of a first wearable dispenser assembly and an identification badge is within a boundary of a zone around a bed; and
     generate a sanitize reminder signal when at least one of the first wearable dispenser assembly and the identification badge is within the zone boundary;
   a user interface device (UID) control module configured to, in response to the sanitize reminder signal, control a user interface device to generate a message reminding a person wearing at least one of the first wearable dispenser assembly and the identification badge to use hand sanitizer before approaching a patient in the bed;
   a dispensing event module configured to:
     determine when a bed dispenser assembly performs a dispensing event by dispensing hand sanitizer; and
     store a date of the dispensing event and a time of the dispensing event,
   wherein the bed zone boundary module is configured to:
     detect when the first wearable dispenser assembly is within the zone boundary;
     detect when a second wearable dispenser assembly is within the zone boundary;
     detect when the identification badge is within the zone boundary; and
     determine which one of the first wearable dispenser assembly, the second wearable dispenser assembly, and the identification badge is closer to the bed dispenser assembly based on a strength of a first signal received from the first wearable dispenser assembly, a strength of a second signal received from the second wearable dispenser assembly, and a strength of a third signal received from the identification badge, and
   wherein the dispensing event module is configured to associate the dispensing event with the one of the first wearable dispenser assembly, the second wearable dispenser assembly, and the identification badge that is closer to the bed at the time of the dispensing event.

2. A system comprising:
   a room identification module configured to generate a room identification signal indicating an identification of a room in a healthcare facility;
   a bed location module configured to:
     receive the room identification signal;
     in response to the room identification signal, associate a first bed with the room identification; and
     store a date on which the first bed is associated with the room identification and a time at which the first bed is associated with the room identification; and
   a bed identification module configured to generate a first bed identification signal indicating an identification of the first bed, wherein the roam identification module is configured to:
     receive the first bed identification signal; and
     determine a location of the first bed within the room based on a strength of the first bed identification signal; and
   further comprising a second bed identification module configured to generate a second bed identification signal indicating an identification of a second bed, wherein the room identification module is configured to:
     receive the second bed identification signal;
     compare a strength of the second bed identification signal to the first bed identification signal; and
     based on the comparison, determine the location of the first bed within the room and a location of the second bed within the room.

3. The system of claim 2 further comprising a bed zone boundary module configured to: detect when at least one of a wearable dispenser assembly and an identification badge is within a boundary of a zone around the first bed; and selectively generate a sanitize reminder signal when at least one of the wearable dispenser assembly and the identification badge is within the zone boundary.

4. A system comprising:
   a room identification module configured to generate a room identification signal indicating an identification of a room in a healthcare facility;
   a bed location module configured to:
     receive the room identification signal;
     in response to the room identification signal, associate a first bed with the room identification; and
     store a date on which the first bed is associated with the room identification and a time at which the first bed is associated with the room identification; and
   a bed zone boundary module configured to:
     detect when at least one of a wearable dispenser assembly and an identification badge is within a boundary of a zone around the first bed; and
     selectively generate a sanitize reminder signal when at least one of the wearable dispenser assembly and the identification badge is within the zone boundary, wherein the bed zone boundary module is configured to generate the sanitize reminder signal when:
- at least one of the wearable dispenser assembly and the identification badge is within the zone boundary; and
- the room ID signal is received.

5. The system of claim 4 wherein the bed zone boundary module is configured to stop generating the sanitize reminder signal when the room ID signal is no longer received.

6. The system of claim 5 wherein the bed zone boundary module is configured to resume generating the sanitize reminder signal when the room ID signal is received for at least a predetermined period.

7. A system comprising:
- a wearable dispenser location module configured to determine a location of a wearable dispenser assembly;
- a dispensing event module configured to:
  - detect when the wearable dispenser assembly performs a dispensing event by dispensing hand sanitizer; and
  - store a date of the dispensing event, a time of the dispensing event, and the location of the wearable dispenser assembly at the time of the dispensing event;
- a temperature probe control module configured to control a temperature probe to measure a temperature of a person wearing the wearable dispenser assembly; and
- a user interface device (UID) control module configured to control a user interface device to display the temperature of the person and the time at which the temperature of the person is measured, wherein the UID control module is configured to prompt the person wearing the wearable dispenser assembly to perform a temperature check when a period that has elapsed since a last temperature check is greater than a predetermined period.

8. The system of claim 7 wherein the UID control module is configured to control the user interface device to display the date and time of the dispensing event and the location of the wearable dispenser assembly at the time of the dispensing event.

9. The system of claim 8 further comprising a tracking module configured to determine when the person wearing the wearable dispenser assembly has made a stop and a duration of the stop, wherein the UID control module is configured to control the user interface device to display the duration of the stop.

10. A system comprising:
- a bed zone boundary module configured to:
  - detect when a first wearable dispenser assembly or identification badge is within a boundary of a zone around a bed;
  - detect when a second wearable dispenser assembly or identification badge is within the zone boundary; and
  - determine which one of (i) the first wearable dispenser assembly or identification badge and (ii) the second wearable dispenser assembly or identification badge is closer to a bed dispenser assembly based on a strength of a first signal received from the first wearable dispenser assembly or identification badge and a strength of a second signal received from the second wearable dispenser assembly or identification badge; and
- a dispensing event module configured to:
  - determine when the bed dispenser assembly performs a dispensing event by dispensing hand sanitizer; and
  - associate the dispensing event with the one of (i) the first wearable dispenser assembly or identification badge and (ii) the second wearable dispenser assembly or identification badge that is closer to the bed at the time of the dispensing event.

11. The system of claim 10 wherein:
the bed zone boundary module is configured to generate a sanitize reminder signal when at least one of (i) the first wearable dispenser assembly or identification badge and (ii) the second wearable dispenser assembly or identification badge is within the zone boundary; and
the system further comprises a user interface device (UID) control module configured to, in response to the sanitize reminder signal, control a user interface device to generate a message reminding a person wearing at least one of (i) the first wearable dispenser assembly or identification badge and (ii) the second wearable dispenser assembly or identification badge to use hand sanitizer before approaching a patient in the bed.

12. The system of claim 10 wherein the dispensing event module is configured to store a date of the dispensing event and a time of the dispensing event.

\* \* \* \* \*